United States Patent
Kuenzer et al.

(10) Patent No.: US 6,844,336 B2
(45) Date of Patent: Jan. 18, 2005

(54) 4-FLUOROALKYL-2H-BENZOPYRANS WITH ANTI-ESTOGENIC ACTIVITY

(75) Inventors: Hermann Kuenzer, Berlin (DE); Rolf Jautelat, Berlin (DE); Ludwig Zorn, Berlin (DE); Christa Hegele-Hartung, Muelheim a. d. Ruhr (DE); Uwe Kollenkirchen, Berlin (DE); Karl-Heinrich Fritzemeier, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/221,553
(22) PCT Filed: Mar. 15, 2001
(86) PCT No.: PCT/EP01/02928
§ 371 (c)(1), (2), (4) Date: Jan. 7, 2003
(87) PCT Pub. No.: WO01/68634
PCT Pub. Date: Sep. 20, 2001

(65) Prior Publication Data
US 2004/0034017 A1 Feb. 19, 2004

(30) Foreign Application Priority Data
Mar. 15, 2000 (DE) .......................... 100 13 782

(51) Int. Cl.[7] .................. A61K 31/35; A61K 31/445; C07D 311/64; C07D 413/12; C07D 405/12
(52) U.S. Cl. ................ 514/212; 514/228.2; 514/233.5; 514/320; 514/422; 514/456; 540/596; 544/62; 544/151; 546/196; 548/525; 549/406
(58) Field of Search ............... 540/596; 544/62, 544/151; 546/196; 548/525; 549/406; 514/212, 228.2, 233.5, 320, 422, 456

(56) References Cited

U.S. PATENT DOCUMENTS 5,254,568 A 10/1993 Kapil et al.
6,060,503 A 5/2000 Labrie et al.

FOREIGN PATENT DOCUMENTS

EP 0470310 2/1992
WO WO 9626201 8/1996
WO WO 9902512 1/1999

OTHER PUBLICATIONS

A. P. Sharma et al., "Structure–Activity–Relationship of Antiestrogens. Effect of the Side Chain and Its Position on the Activity of 2,3–Diaryl–2H–1–benzopyrans," J. Med. Chem., 1990, pp. 3216–3222 and pp. 3219–3220, vol. 33, XP002170868.

*Primary Examiner*—Bernard Dentz
(74) *Attorney, Agent, or Firm*—Millen White Zelano & Branigan, P.C.

(57) ABSTRACT

This invention describes the new 4-fluoroalkyl-2H-benzopyrans of general formula I,

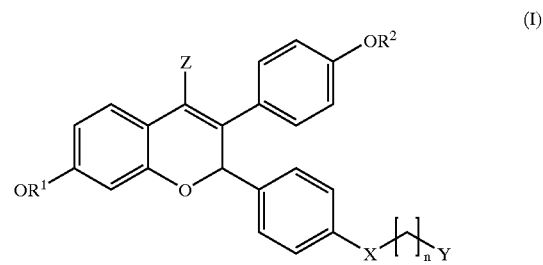

in which
Z is a straight-chain or branched-chain alkyl group with up to 5 carbon atoms that is fluorinated in at least one place, preferably a trifluoromethyl group, and $R^1$, $R^2$, X, Y and n have the meanings that are indicated in the description.

The new compounds have at their disposal strong antiestrogenic action. In addition, they can have at their disposal estrogenic action that occurs in a tissue-selective manner. They can be used for the production of pharmaceutical agents, especially for the treatment of estrogen-dependent diseases and tumors and pharmaceutical agents for hormone replacement therapy (HRT) as well as for the prevention and treatment of osteoporosis.

36 Claims, No Drawings

4-FLUOROALKYL-2H-BENZOPYRANS WITH ANTI-ESTOGENIC ACTIVITY

This application was the National Stage of International Application No. PCT/EPO1/02928 filed 15 Mar. 2001.

This invention relates to the 4-fluoroalkyl-2H-benzopyrans of general formula I

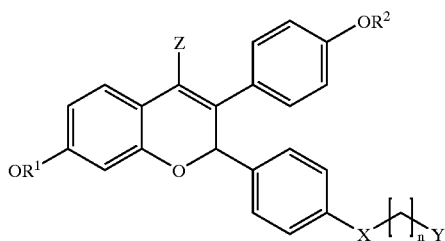

in which
R$^1$ and R$^2$, independently of one another, mean a hydrogen atom, a straight-chain or branched-chain alkyl group with up to 5 carbon atoms, a straight-chain or branched-chain alkanoyl group with up to 5 carbon atoms or a benzoyl group,
X means an oxygen or sulfur atom or a methylene group,
n means 2, 3 or 4,
Y means a group —NR$^3$R$^4$, whereby
R$^3$ and R$^4$, independently of one another, mean a hydrogen atom, a straight-chain or branched-chain, optionally partially fluorinated alkyl alkenyl or alkenyl radical with up to 10 carbon atoms, which can be interrupted by one to three heteroatoms —O— and —S— and groupings —NR$^5$—, in which R$^5$ is a hydrogen atom or a straight-chain or branched-chain alkyl group with up to 5 carbon atoms, an aryl or heteroaryl radical that is optionally substituted in one or two places, a C$_3$–C$_{10}$-cycloalkyl radical that is optionally substituted in one or two places, a C$_4$–C$_{15}$-cycloalkylalkyl radical that is optionally substituted in one or two places, a C$_7$–C$_{20}$-aralkyl radical that is optionally substituted in one or two places, a heteroaryl-C$_1$-C$_8$-alkyl radical that is optionally substituted in one or two places or an optionally substituted aminoalkyl radical, a biphenylene radical or a radical of formula —C(O)R$^6$, in which R$^6$ can have the meanings indicated above for R$^3$ or R$^4$, or else
R$^3$ and R$^4$ together with the nitrogen atom can contain as a ring member a 5- to 7-membered, saturated or unsaturated heterocyclic ring, which in addition can contain an oxygen or sulfur atom or a nitrogen group =N— or —NR$^7$—, in which R$^7$ is a hydrogen atom or a straight-chain or branched-chain alkyl group with up to 5 carbon atoms, and
Z means a straight-chain or branched-chain alkyl group with up to 5 carbon atoms that is fluorinated in at least one place,
as well as their physiologically compatible addition salts with organic and inorganic acids.

In addition to these compounds of general formula I and their physiologically compatible addition salts with organic and inorganic, acids, this invention relates to these compounds of general formula I including the pharmaceutical preparations that contain addition salts as well as their use for the production of pharmaceutical agents.

For forming acid addition salts, inorganic and organic acids, as they are known to one skilled in the art for forming physiologically compatible salts, are suitable. As addition salts with acids, especially hydrochlorides, hydrobromides, acetates, citrates, oxalates, tartrates and the methanesulfonates can be cited.

An alkyl radical R$^1$, R$^2$, R$^5$ or R$^7$ is a straight-chain or branched-chain alkyl group with up to 5 carbon atoms, such as, for example, methyl, ethyl, propyl, isopropyl, butyl, isobutyl, tert-butyl, pentyl, isopentyl or neopentyl.

The alkanoyl groups that are possible as R$^1$ or R$^2$ are to contain 1 to 5 carbon atoms, whereby formyl, acetyl, propionyl and isopropionyl groups are preferred.

As alkyl groups R$^3$ and R$^4$, straight-chain or branched-chain alkyl groups with up to 10 carbon atoms can be considered, such as, for example, methyl, ethyl, propyl, isopropyl, butyl, isobutyl, tert-butyl, pentyl, isopentyl, neopentyl, heptyl, hexyl, or decyl.

The latter can have up to 3 unsaturations (double and/or triple bonds).

Alkyl groups R$^3$ and R$^4$ can be partially or completely fluorinated or substituted.

As a partially or completely fluorinated straight-chain or branched alkyl group with up to 10 carbon atoms, for example, the monofluoromethyl group, difluoromethyl group, trifluoromethyl group, pentafluoroethyl group, 2,2,2-trifluoroethyl group, 4,4,4-trifluorobutyl group, 3,3,4,4,4-pentafluorobutyl group, 4,4,5,5,5-pentafluoropentyl group or the nonafluorobutyl group can be mentioned.

The latter can also have up to 3 unsaturations (double and/or triple bonds).

For aryl radical R$^3$ or R$^4$ and the (hetero)aryl radical within (hetero)arylalkyl radical R$^3$ or R$^4$, the following radicals that are optionally substituted in one or more places can be:

a monocyclic, carbocyclic radical, for example the phenyl radical;

a monocyclic, heterocyclic radical, for example the thienyl, furyl, pyrrolyl, imidazolyl, pyrazolyl, pyridyl, pyrazinyl, pyrimidinyl, pyridazinyl, thiazolyl, oxazolyl, furazanyl, pyrrolinyl, imidazolinyl, pyrazolinyl, thiazolinyl, triazolyl, tetrazolyl radical, specifically all possible isomers relative to the positions of the heteroatoms;

a condensed carbocyclic radical, for example the naphthyl or phenanthrenyl radical, a condensed radical, which consists of carbocyclic and heterocyclic radicals, for example the benzofuranyl, benzothienyl, benzimidazolyl, benzothiazolyl, naphtho[2,3-b]thienyl, thianthrenyl, isobenzofuranyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, acridinyl, phenazinyl, phenothiazinyl, phenoxazinyl, indolinyl, isoindolinyl, imidazopyridyl, imidazopyrimidinyl or a condensed polyheterocyclic system, for example furo[2,3-b]pyrrole or thieno[2,3-b]furan.

As a cycloalkyl group for substituted R$^3$ and R$^4$, substituted and unsubstituted radicals with 3 to 10 carbon atoms are suitable: mainly the cyclopropyl group and the cyclopentyl group can be cited, and as an alkylcycloalkyl group, the methylcyclopropyl group and the methylcyclopentyl group can be cited.

The C$_7$-C$_{20}$-aralkyl radicals in R$^3$ and R$^4$ can contain in the ring up to 14 C atoms, preferably 6 to 10 C atoms, and in the alkyl chain 1 to 8, preferably 1 to 4 C atoms.

As a heteroaryl part, a heteroaryl-$C_1$–$C_8$-alkyl radical in $R^3$ and $R^4$ has one of the already mentioned heteroaryl radicals; the alkyl chain comes with 1 to 8, preferably 1 to 4 C atoms.

As aralkyl radicals, for example, benzyl, phenylethyl, phenylpropyl, naphthylmethyl, and naphthylethyl are considered, and as heteroarylalkyl radicals, furylmethyl, thienylethyl, and pyridylpropyl are considered.

The rings can be substituted in one or two places.

If $R^3$ and $R^4$ with the nitrogen atom, to which they are bonded, contain a saturated or unsaturated heterocyclic compound with 5 or 6 chain links, which optionally contains one or two additional heteroatoms, selected from nitrogen, oxygen and sulfur, this is in particular a pyrrolidine, piperidine, morpholine or piperazine ring.

The following radicals are mentioned primarily as substituent Y: the piperidine, pyrrolidine, hexamethylenimino, pyrrolidine, dimethylamino, diethylamino, dipropylalmino, N-methyl-N-phenethylamino, N-methyl-N-(3-phenylpropyl)amino, N-butyl-N-ethylamino, thiomorpholino, morpholino, N-methyl-N-pentylaimino, N-isobutyl-N-methylamino, N-benzyl-N-methylamino, and N-butyl-N-methyalmino groups.

Fluorinated alkyl radical Z is a straight-chain alkyl radical with 1 to 5 carbon atoms that is fluorinated in at least one place or a branched alkyl radical with 3, 4 or 5 carbon atoms that is fluorinated in at least one place.

As representatives of Z, the monofluoromethyl, difluoromethyl, trifluoromethyl, pentafluoroethyl, 2,2,2-trifluoroethyl, n- and i-heptafluoropropyl, 4,4,4-trifluorobutyl, 3,3,4,4,4-pentafluorobutyl, 2,2,2-trifluoroethyl, 4,4,4-trifluorobutyl, 3,3,4,4,4-pentafluorobutyl, 4,4,5,5,5-pentafluoropentyl or the nonafluorobutyl group can be mentioned.

As substituted of radicals $R^3$ and $R^4$, the following substituted are suitable, whereby the radicals can be substituted with these substituents in one or two places in the same way or differently:

halogen atoms: fluorine, chlorine, bromine, iodine;

amino-, mono($C_{1-8}$-alkyl)- or di($C_{1-8}$-alkyl)amino, whereby both alkyl groups are identical or different, especially methylamino or ethylamino, dimethylamino, diethylamino or methylethylamino; di(aralkyl)amino, whereby both aralkyl groups are identical or different;

hydroxyl groups;

carboxyl groups that are free, esterified or present in the form of a salt: esterified with a carboxycarbonyl group, for example methoxycarbonyl or ethoxycarbonyl;

as a salt, for example, in the form of sodium or potassium salt;

alkyl groups with 1 to 8 carbon atoms, such as, for example, the methyl, ethyl, n- or iso-propyl, n-, iso- or tert-butyl group, optionally substituted with one or more halogen atoms, for example with fluorine such as the trifluoromethyl group or the pentafluoroethyl group;

oxo-, azido, cyano, nitro or formyl groups;

acyl groups such as acetyl, propionyl, butyryl, benzoyl;

acyloxy groups such as acetoxy, radicals of Formula —O—CO—$(CH_2)_n$—COOH with n 1 to 5;

$C_1$–$C_4$ alkoxy groups, such as, for example, methoxy, ethoxy, propoxy, isopropoxy, butoxy;

alkylthio groups, for example methylthio, ethylthio, propylthio, isopropylthio, butylthio, all optionally fluorinated;

carbamoyl groups;

alkenyl groups, for example, vinyl, propenyl;

alkinyl groups, for example ethinyl, propinyl;

$C_6$-$C_{12}$-aryl groups, such as phenyl, furyl, thienyl, which in turn can be substituted in one to three places.

As substituents for the aryl, heteroaryl, aralkyl and heteroarylalkyl radicals, in particular a -trifluoromethyl-, pentafluoroethyl-, trifluoromethylthio-, methoxy-, ethoxy-, nitro-, cyano-, halogen- (fluorine, chlorine, bromine, iodine), hydroxy-, amino-, mono($C_{1-8}$-alkyl)- or di($C_{1-8}$-alkyl)amino, whereby both alkyl groups are identical or different, di(aralkyl)amino, whereby both aralkyl groups are identical or different, or the 1-methoxyacetylamino radical can be mentioned.

Free hydroxy groups-in the compounds of general formula I can be modified functionally, for example by etherification or esterification. As ether and acyl radicals, the radicals that are known to one skilled in the art, such as, e.g., the methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, methyl, tert-butyl, benzyl, para-nitrobenzyl, para-methoxybenzyl, formyl, acetyl, propionyl, isopropionyl, butyryl, pivalyl, and benzoyl radicals, are suitable. There is a survey in, e.g., "Protective Groups in Organic Synthesis" Theodora W. Green, John Wiley and Sons).

A variant of the invention provides that $R^1$ and $R^2$ both stand for hydrogen.

According to another variant, $R^1$ and $R^2$ each stand for a methyl group.

In another variant, $R^1$ and $R^2$ are each a pivaloyl group.

Link X is preferably an oxygen or sulfur atom.

In a like manner, index n can assume the value 2, 3 or 4.

Z primarily stands for a trifluoromethyl group; a perfluoroethyl group is also preferred.

The compounds of general formula I have a center of asymmetry on carbon atom 2 of the 2H-benzopyran skeleton.

The invention relates to both the racemic mixtures of the compounds of general formula I and the separate optical isomers as well as the non-racemic mixtures of the optical isomers.

The racemates that accumulate in the synthesis of the compounds of general formula I according to the invention can be separated according to methods that are known to one skilled in the art, for example with use of HPLC on a chiral stationary phase.

This separation into the optical antipodes can be carried out in the stage of the final compound of general formula I, as this is described in Example 1, or else in an earlier racemic stage.

A derivatization or functionalization of the free dihydroxy compound into the esters ($R^1$ and/or $R^2$ alkanoyl or benzoyl) or ethers ($R^1$ and/or $R^2$=alkyl) can be carried out on racemic mixtures or on the separate isomers.

Functional groups $R^1$ and/or $R^2$, especially for the case that the two substituents are to be different, can also be introduced as early as during the creation of the intermediate stage of 2,3-dihydro-4H-1-benzopyran-4-one.

This invention relates in particular to the compounds (+)-7-Hydroxy-3-(4'-hydroxyphenyl)-2-[4"-(2'"-piperidin-1-ylethoxy)-phenyl]-4-(trifluoromethyl)-2H-1-benzopyran (−)-7-Hydroxy-3-(4'-hydroxyphenyl)-2-[4"-(2'"-piperidin-1-ylethoxy)-phenyl]-4-(trifluoromethyl)-2H-1-benzopyran (+)-7-pivaloyloxy-3-(4'-pivaloyloxyphenyl)-4-trifluoromethyl-2-(4"-(2'"-piperidino-ethoxy)phenyl)-2H-benzopyran (−)-7-pivaloyloxy-3-(4'-pivaloyloxyphenyl)-4-trifluoromethyl-2-(4"-(2'"-piperidinoethoxy)-phenyl)-2H-benzopyran 2-[4"-(2'"-dimethylaminoethoxy)-phenyl]-7-hydroxy-3-(4'-hydroxyphenyl)-4-(trifluoromethyl)-2H-1-benzopyran 2-[4"-(2'"-diethylaminoethoxy)-phenyl]-7-hydroxy-3-(4'-hydroxyphenyl)-4-(trifluoromethyl)-2H-1-benzopyran 7-hydroxy-3-(4'-hydroxyphenyl)-2-[4"-(2'"-N-methyl-N-phenethylaminoethoxy)-phenyl]-4-(trifluoromethyl)-2H-1-benzopyran 7-hydroxy-3-(4'-hydroxyphenyl)-2-{4"-[2'"-N-methyl-N-(3""-phenylpropyl)aminoethoxy]-phenyl}-4-(trifluoromethyl)-2H-1-benzopyran 2[4"-(2'"-N-butyl-N-ethylaminoethoxy)-phenyl]-7-hydroxy-3-(4'-hydroxyphenyl)-4-(trifluoromethyl)-2H-1-benzopyran 7-hydroxy-3-(4'-hydroxyphenyl)-2-[4"-(thiomorpholin-1-ylethoxy)-phenyl]-4-(trifluoromethyl)-2H-1-benzopyran 7-hydroxy-3-(4'-hydroxpheny)-2-[4"-(2'"-pyrrolidin-1-ylethoxy)-phenyl]-4-(trifluoromethyl)-2H-1-benzopyran 7-hydroxy-3-(4'-hydroxyphenyl)-2-[4"-(2'-morpholin-1-ylethoxy)-phenyl]-4-(trifluoromethyl)-2H-1-benzopyran 7-hydroxy-3-(4'-hydroxyphenyl)-2-[4"-(2'"-N-methyl-N-pentylaminoethoxy)-phenyl]-4-(trifluoromethyl)-2H-1-benzopyran 7-hydroxy-3-(4'-hydroxyphenyl)-2-[4"-(2'"-N-isobutyl-N-methylaminoethoxy)-phenyl]-4-(trifluoromethyl)-2H-1-benzopyran 2-[4"-(2'"-N-benzyl-N-methylaminoethoxy)-phenyl]-7-hydroxy-3-(4'-hydroxyphenyl)-4-(trifluoromethyl)-2H-1-benzopyran 2-[4"-(2'"-N,N-di-n-propylaminoethoxy)-phenyl]-7-hydroxy-3-(4'-hydroxyphenyl)-4-(trifluoromethyl)-2H-1-benzopyran 2-[4"-(2'"-hexamethylenimin-1-ylethoxy)-phenyl]-7-hydroxy-3-(4'-hydroxyphenyl)-4-(trifluoromethyl)-2H-1-benzopyran 2-[4"-(2'"-N-butyl-N-methylaminoethoxy)-phenyl]-7-hydroxy-3-(4'-hydroxyphenyl)-4-(trifluoromethyl)-2H-1-benzopyran 7-hydroxy-3-(4'-hydroxyphenyl)-2-[4"-(3'"-piperidin-1-ylpropoxy)-phenyl]-4-(trifluoromethyl)-2H-1-benzopyran 2-[4"-(3'"-N-dimethylaminopropoxy)-phenyl]-7-hydroxy-3-(4'-hydroxyphenyl)-4-(trifluoromethyl)-2H-1-benzopyran 2-[4"-(3'"-N-diethylaminopropoxy)-phenyl]-7-hydroxy-3-(4'-hydroxyphenyl)-4-(trifluoromethyl)-2H-1-benzopyran 7-hydroxy-3-(4'-hydroxyphenyl)-2-[4"-(3'"-N-methyl-N-phenethylaminopropoxy)-phenyl]-4-(trifluoromethyl)-2H-1-benzopyran 7-hydroxy-3-(4'-hydroxyphenyl)-2-{4"-[3'"-N-methyl-N-(3""-phenylpropyl)aminopropoxy]-phenyl}-4-(trifluoromethyl)-2H-1-benzopyran 2-[4"-(3'"-N-butyl-N-ethylaminopropoxy)-phenyl]-7-hydroxy-3-(4'-hydroxyphenyl)-4-(trifluoromethyl)-2H-1-benzopyran 7-hydroxy-3-(4'-hydroxyphenyl)-2-[4"-(3'"-thiomorpholin-1-ylpropoxy)-phenyl]-4-(trifluoromethyl)-2H-1-benzopyran 7-hydroxy-3-(4'-hydroxyphenyl)-2-[4"-(3'"-pyrrolidin-1-ylpropoxy)-phenyl]-4-(trifluoromethyl)-2H-1-benzopyran 7-hydroxy 3-(4'-hydroxyphenyl)-2-[4"-(3'"-morpholin-1-ylpropoxy)-phenyl]-4-(trifluoromethyl)-2H-1-benzopyran 7-hydroxy-3-(4'-hydroxyphenyl)-2-[4"-(3'"-N-methyl-N-pentylaminopropoxy)-phenyl]-4-(trifluoromethyl)-2H-1-benzopyran 7-hydroxy-3-(4'-hydroxyphenyl)-2-[4"-(3'"-N-isobutyl-N-methylaminopropoxy)-phenyl]-4-(trifluoromethyl)-2H-1-benzopyran 2-[4"-(3'"-N-benzyl-N-ethylaminopropoxy)-pheny]-7-hydroxy-3-(4'-hydroxyphenyl)-4-(trifluoromethyl)-2H-1-benzopyran 2-[4"-(3'"-N,N-di-n-propylaminopropoxy)-phenyl]-7-hydroxy-3-(4'-hydroxyphenyl)-4-(trifluoromethyl)-2H-1-benzopyran 2-[4"-(3 '"-hexamethylenimin-1-ylpropoxy)-phenyl]-7-hydroxy-3-(4'-hydroxyphenyl)-4-(trifluoromethyl)-2H-1-benzopyran 2-[4"-(3'"-N-butyl-N-methyl aminopropoxy)-phenyl]-7-hydroxy-3-(4'-hydroxyphenyl)-4-(trifluoromethyl)-2H-1-benzopyran 7-hydroxy-3-(4'-hydroxyphenyl)-2-[4"-(4'"-piperidin-1-ylbutoxy)-phenyl]-4-(trifluoromethyl)-2H-1-benzopyran 2-[4"-(4'"-N-dimethylaminobutoxy)-phenyl]-7-hydroxy-3-(4'-hydroxyphenyl)-4-(trifluoromethyl)-2H-1-benzopyran 2-[4"-(4'"-N-diethylaminobutoxy)-phenyl]-7-hydroxy-3-(4'-hydroxyphenyl)-4-(trifluoromethyl)-2H-1-benzopyran 7-hydroxy-3-(4'-hydroxyphenyl)-2-[4"-(4'"-N-methyl-N-phenethylaminobutoxy)-phenyl]-4-(trifluoromethyl)-2H-1-benzopyran 7-hydroxy-3-(4'-hydroxyphenyl)-2-{4"-[4'"-N-methyl-N-(3 ""-phenylpropyl)-aminobutoxy]-phenyl}-4-(trifluoromethyl)-2H-1-benzopyran 2-[4"-(4'"-N-butyl-N-ethylaminobutoxy)-phenyl]-7-hydroxy-3-(4'-hydroxyphenyl)-4-(trifluoromethyl)-2H-1-benzopyran 7-hydroxy-3-(4'-hydroxyphenyl)-2-[4-(4''-thiomorpholin-1-ylbutoxy)-phenyl]-4-(trifluoromethyl)-2H-1-benzopyran 7-hydroxy-3-(4'-hydroxyphenyl)-2-[4"-(4'"-pyrrolidin-1-ylbutoxy)-phenyl]-4-(trifluoromethyl)-2H-1-benzopyran 7-hydroxy-3-(4'-hydroxyphenyl)-2-[4"-(4''-morpholin-1-ylbutoxy)-phenyl]-4-(trifluoromethyl)-2H-1-benzopyran 7-hydroxy-3-(4'-hydroxyphenyl)-2-[4"-(4'"-N-methyl-N-pentylaminobutoxy)-phenyl]-4-(trifluoromethyl)-2H-1-benzopyran 7-hydroxy-3-(4'-hydroxyphenyl)-2-[4"-(4'"-N-isobutyl-N-methylaminobutoxy)-phenyl]-4-(trifluoromethyl)-2H-1-benzopyran 2-[4"-(4'"-N-benzyl-N-methylaminobutoxy)-phenyl]-7-hydroxy-3-(4'-hydroxyphenyl)-4-(trifluoromethyl)-2H-1-benzopyran 2-[4"-(4'"-N,N-di-n-propylaminobutoxy)-phenyl]-7-hydroxy-3-(4'-hydroxyphenyl) -4-(trifluoromethyl)-2H-1-benzopyran 2-[4"-(4'"-hexamethylenimin-1-ylbutoxy)-phenyl]-7-hydroxy-3-(4'-hydroxyphenyl) -4-(trifluoromethyl)-2H-1-benzopyran 2-[4"-(4'"-N-butyl-N-methylaminobutoxy)-phenyl]-7-hydroxy-3-(4'-hydroxyphenyl)-4-(trifluoromethyl)-2H-1-benzopyran (+)-7-methoxy-3-(4'-methoxyphenyl)-2-[4"-(2'"-piperidin-1-ylethoxy)-phenyl]-4-(trifluoromethyl)-2H-1-benzopyran (−)-7-methoxy-3-(4'-methoxyphenyl)-2-[4"-(2''-piperidin-1-ylethoxy)-phenyl]-4-(trifluoromethyl)-2H-1-benzopyran 7-hydroxy-3-(4'-hydroxyphenyl)-2-[4"-(3'"-piperidin-1-yl-1-thiapropyl) -phenyl]-4-(trifluoromethyl)-2H-1-benzopyran.

The compounds of general formula I represent compounds with strong antiestrogenic action.

Compounds with antiestrogenic properties, i.e., substances with inhibiting actions relative to estrogens, have already been described extensively.

As the compounds structurally coming closest to these compounds of general formula I, the compounds that are known from WO 93/10741 and especially the compounds that are known from WO 96/26201 can be considered. The known compounds are described as estrogen antagonists and/or compounds that suppress estrogen biosynthesis. These known compounds have the building block of 2H-benzopyran like the compounds of general formula I according to the invention. In the 4-position of the skeleton, however, the known compounds cannot carry any perfluoroalkyl group.

In addition, 2,3-diaryl-2H-1-benzopyrans, which are also described in J. Med. Chem. 1990, 33, 3210–3216 and 3216–3222 as well as 3222–3229 and which as possible substituents can have only one hydrogen atom in 4-position, are to be used as prior art.

The compounds according to the invention are either pure antiestrogens (estrogen antagonists) or so-called partial agonists, i.e., antiestrogens with estrogenic partial action such as tamoxifen, raloxifene or EM 800.

Unlike tamoxifen, in the case of partial agonists of general formula I, the tissue selectivity of the agonistic, estrogenic action thereof is more strongly pronounced. In particular, the agonistic action occurs on bone, in the cardiovascular system and in the CNS (central nervous system), while little or no agonistic action occurs in the uterus and in the breast. Compounds with such a profile are designated as Selective Estrogen Receptor Modulators (SERMs) (Structure-Activity Relationships of Selective Estrogen Receptor Modulators: Modifications to the 2-Arylbenzothiophene Core of Raloxifene, T. A. Grese et al., J. Med. Chem. 1997, 40, 146–167). The most prominent representative of this compound class is the raloxifene, which is allowed in the meantime as a medication for the prevention and the treatment of postmenopausal osteoporosis.

The compounds that are preferred according to this invention are tissue-selective estrogens (SERMs).

The compounds of general formula I represent more strongly antiestrogenically active compounds in the breast cancer cell lines (for example, in MCF-7 cell lines and in T47D cell lines).

The EM 800 [(#)-7-pivaloyloxy-3-(4'pivaloyloxyphenyl)-4-methyl-2-(4"-(2"piperidinoethoxy)phenyl)-2H-benzopyran] that has become known only recently as a selective estrogen {J. Steroid Biochem. & Mol. Biol., 69, pp. 51–84, 1999} had originally been described in WO 96/26201 as a pure antiestrogen. This bispivalate is a Pro-drug of the free dihydroxy compound.

In contrast to EM 800, in the case of partial agonists of general formula I, the tissue-selective estrogenic action is generally more strongly pronounced, whereby the antagonistic action, however, is at least comparable or better to be able to exert the protective effect of the antiestrogen on the breast and the uterus. The tissue-selective estrogens of this invention are consequently compounds with a better balanced profile of action with respect to estrogenic and antiestrogenic action.

Otherwise, the compounds of general formula I with a fluorinated alkyl group, especially a trifluoromethyl group, in 4-position according to this application in comparison to the already known EM 800, are distinguished by a higher air stability. The new compounds can therefore be formulated more simply than pharmaceutical preparations. This circumstance also has an advantageous effect on the shelf life of finish-formulated pharmaceutical preparations. A comparable shelf life of the pharmaceutical preparations according to the invention in comparison to the preparations that contain, for example, EM 800 can be achieved with a less expensive formulation technique and galenical form of formulation.

Pharmacological Study of the Compounds, According to the Invention

The influence of the compounds according to the invention on the uterus was examined in the uterus growth test (estrogenic action) and in the antiuterus growth test (antiestrogenic action), both performed on infant rats.

Estrogenic/Antiestrogenic Action In Vivo

Uterus Growth Test on Infant Rats (n=5 Animals/Group)

In infant animals, both uterus and vagina show a weight increase based on the estrogenic action in their treatment with an estrogenically active substance. In the uterus, this also results under estrogenic action in a proliferation and increase in the height of the luminal epithelium. Immature, intact rats (body weight 40–50 g) receive the substance s.c. over 3 days (d1–d3). On day 4 (d4), the animals are sacrificed with $CO_2$. The uteri are prepared outside and weighed. A piece of the uterus, preferably a uterine horn, is fixed in formaldehyde for histological evaluation and embedded in paraffin The stimulation of the organ weights (relative to mg/100 g of body weight) and the epithelial height is indicated in percentage stimulation in comparison to the reference compound 17β-estradiol (substitution dose of $E_2$ 0.3 μg/animal).

The compounds according to the invention have little or no stimulating action on the uterus.

Antiuterus Growth Test on Infant Rats (n=5 Animal/Group)

The uterus of infant estrogen-substituted rats can be used as a test model to detect a direct action of substances with antiestrogenic properties. The parameter of the estrogenic action is the uterus growth that is induced by estradiol in infant rats and that is inhibited by simultaneous administration of a substance with antiestrogenic action.

The test substances are treated s.c. on 3 successive days (d1–d3) in combination with a substitution dose of 0.3 μg/animal/day of 17β-estradiol. 17β-Estradiol by itself is used as a positive control, and the vehicle group is used as a negative control. On day 4 (d4), the animals are sacrificed, and uteri and vaginae are prepared outside and weighed. The organ weights are converted into mg/100 g of body weight, then the mean and the standard deviation for each dosage are calculated. The inhibition of the uterus or vaginal growth that is induced by 17β-estradiol is indicated as inhibition in %. The compounds according to the invention have for the most part a clearly pronounced inhibition of the uterus growth that is induced by 17β-estradiol.

With respect to their action on the uterus, the compounds according to the invention are thus superior to the compounds of the prior art in terms of this invention to the extent that they have little or even no estrogenic action on this organ.

Bone Studies

Method

Three-month-old female rats are ovariectomized and treated once daily with the test compound immediately after the operation for 28 days. The administration is carried out subcutaneously in arachis oil/ethanol or it is carried out perorally. The animals are sacrificed on the day after the last administration, and tibiae as well as uteri are removed. The uteri are weighed, fixed and worked up for histological studies. The determination of the bone density is carried out ex vivo on prepared long bones using pQCT (quantitative computer tomography). The measurements are performed at a distance of 4–6 mm from the ball of the joint of the proximal tibia.

By the ovariectomy, the density of the trabecular bone in the measured area is reduced by about 400 mg of $Ca^{2+}/cm^3$ to about 300 mg of $Ca^{2+}/cm^3$. By the treatment with a compound of general formula I according to this invention (dosage of 0.1 mg/kg/animal/day p.o.), the degradation of the bone density in the proximal tibia is prevented or inhibited.

In this test, (+)-7-hydroxy-3-(4'-hydroxyphenyl)-2-[4''-(2'''-piperidin-1-ylethoxy)-phenyl]-4-(trifluoromethyl)-2H-1-benzopyran produces a bone protection in comparison to the control that was subjected to a sham operation of 73%.

The invention also relates to pharmaceutical preparations that contain at least one compound of general formula I (or physiologically compatible addition salts with organic and inorganic acids thereof), and the use of these compounds for the production of pharmaceutical agents, especially for the indications below, namely for the treatment of estrogen-dependent diseases and tumors and pharmaceutical agents for hormone replacement therapy (HRT) as well as for the prevention and treatment of osteoporosis.

The compounds according to the invention and the acid addition salts are suitable for the production of pharmaceutical compositions and preparations. As active ingredients, the pharmaceutical compositions or pharmaceutical agents contain one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 and ff.; issued by Czetsch-Lindenwald, Hilfsstoffe für Pharmazie und angrenzende Gebiete [Adjuvants for Pharmaceutics and Related Fields]; Pharm. Ind. Number 2, 1961, pages 72 and ff.; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields] Cantor K G, Aulendorf in Württemberg 1971.

The compounds can be administered orally or parenterally, for example intraperitoneally, intramuscularly, subcutaneously, percutaneously, nasally or via the lungs. The compounds can also be implanted in the tissue.

The amount of the compounds that is to be administered fluctuates within a wide range and can cover any effective amount. Based on the condition to be treated and the type of administration, the amount of administered compound can be 0.001 to 25 mg/kg of body weight, preferably 0.01 to 5 mg/kg of body weight, per day.

In humans, this corresponds to a daily dose of 0.05 to 1250 mg. The preferred daily dosage in humans is 0.5 to 250 mg. This applies especially for tumor therapy.

A dosage unit contains 0.025 to 250 mg of one or more compounds of general formula I according to the invention.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc. The individual dosage units for the oral administration can contain, for example, 5 to 500 mg of active ingredient.

To achieve a better bio-availability of the active ingredient, the compounds can also be formulated as cyclodextrin clathrates. For this purpose, the compounds are reacted with α-, β- or γ-cyclodextrin or derivatives of the latter (PCT/EP95/02656).

For parenteral administration, the active ingredients can be dissolved or suspended in a physiologically compatible diluent. As diluents, very often oils are used with or without the addition of a solubilizer, a surfactant, a suspending agent or emulsifier. Examples of oils that are used are olive oil, peanut oil, cottonseed oil, soybean oil, castor oil and sesame oil.

The compounds of general formula I can also be formulated in the form of a solution that is intended for oral administration and that in addition to the active compound of general formula I contains a) a pharmaceutically compatible oil and/or b) a pharmaceutically compatible lipophilic surfactant and/or c) a pharmaceutically compatible hydrophilic surfactant and/or d) a pharmaceutically compatible water-miscible solvent.

In this respect; reference is made in addition to WO 97/21440.

The compounds can also be used in the form of a depot injection or an implant preparation, which can be formulated in such a way that a delayed release of active ingredients is made possible.

As inert materials, implants can contain, for example, biodegradable polymers or synthetic silicones, such as, for example, silicone gum. In addition to the percutaneous administration, the active ingredients can be worked into, for example, a plaster.

For the production of intravaginal systems (e.g., vaginal rings) or intrauterine systems (e.g., pessaries, coils, IUDs, MIRENA[(R)]) that are charged with the active compounds of general formula I for local administration, various polymers, such as, for example, silicon polymers, ethylene vinyl acetate, polyethylene or polypropylene, are suitable.

According to the invention, the compounds of general formula I can also be encapsulated with liposomes.

The compounds according to the invention, especially if they are pure antiestrogens, are suitable for the therapy of estrogen-dependent diseases, for example breast cancer (second-line therapy of the tamoxifen-resistant breast cancer; for adjuvant treatment of breast cancer instead of tamoxifen), endometrial carcinoma, prostate cancer, pro static hyperplasia, anovulatory infertility and melanoma.

In addition, the pure antiestrogens of general formula I can be used as components in the products that are described in EP 346 014 B1, which contain an estrogen and a pure antiestrogen, specifically for simultaneous, sequential or separate use for the selective estrogen therapy of peri- or postmenopausal women.

The compounds of general formula I, especially if they are pure antiestrogens, can be used together with antigestagens (competitive progesterone antagonists) for treatment of hormone-dependent tumors (EP 310 542 A).

Other indications, in which the compounds of the general formula can be used, are male hair loss, diffuse alopecia, alopecia caused by chemotherapy as well as hirsutism (Hye-Sun Oh and Robert C. Smart, Proc. Natl. Acad. Sci. USA, 93-(1996) 12525–12530.

In addition, the compounds of general formula I can be used for the production of medications for treating endometriosis and endometrial carcinomas.

The compounds of general formula I can also be used for the production of pharmaceutical compositions for male and female birth control (male birth control: DE-A 195 10 862.0).

The compounds of general formula I, which are tissue-selective estrogens, can be used both after oral and parenteral administration, for the following indications:

Alleviation of the symptoms of male menopause and female menopause, i.e., for male and female hormone replacement therapy (HRT), specifically both for prevention and for treatment; for treatment of the symptoms that accompany a dysmenorrhea; treatment of dysfunctional uterine bleeding; treatment of acne; prevention and treatment of cardiovascular diseases; treatment of hypercholesteremia and hyperlipidemia; prevention and treatment of arteriosclerosis; for inhibiting the proliferation of arterial smooth muscle cells; for treatment of the respiratory distress syndrome in newborns; treatment of primary pulmonary high blood pressure; for prevention and treatment of osteoporosis (Black, L. J.; Sato, M.; Rowley, E. R.; Magee, D. E.; Bekele, A.; Williams, D. C.; Cullinan, G. J.; Bendele, R.; Kauffman, R. F.; Bensch, W. R.; Frolik, C. A.; Termine, J. D and Bryant, H. U.: Raloxifene [LY 139481 HCl] Prevents Bone Loss and Reduces Serum Cholesterol without Causing Uterine Hypertrophy in Ovariectomized Rats; J. Clin. Invest. 93: 63–69, 1994); for prevention of bone loss in postmenopausal women, in women who have undergone hysterectomies or in women who were treated with LHRH agonists or antagonists; inhibition of sperm maturation; treatment of rheumatoid arthritis; for prevention of Alzheimer's disease and other neurodegenerative diseases; treatment of endometriosis; treatment of myomas; treatment of myomas and endometriosis in combination with LHRH analogs; treatment of hormone-dependent tumors, e.g., of breast cancer, treatment of prostatic diseases, especially prevention and treatment of prostatic hyperplasia.

In addition, the compounds according to the invention, based on their pharmacological profile, are suitable both for male and female contraception.

The compounds can also be used in combination with the natural Vitamin D3 or with calcitriol analogs or other compounds that promote bone formation, e.g., fluorides, BMPs, statins, etc., for bone formation, or as a supporting therapy to therapies that cause a bone mass loss (for example therapy with glucocorticoids, chemotherapy).

Finally, the compounds of general formula I can be used in connection with progesterone receptor antagonists or in connection with pure estrogens, specifically especially for use in hormone replacement therapy and for treatment of gynecological disorders and for female birth control.

A therapeutic product that contains an estrogen and a pure antiestrogen for simultaneous, sequential or separate use of the selective estrogen therapy of perimenopausal or postmenopausal conditions is already described in EP-A 0 346 014.

The compounds of general formula I according to the invention can be produced as described in the examples. By an analogous procedure using homologous reagents in the reagents described in the examples, all compounds of general formula I can be obtained.

Thus other compounds according to the invention can also be produced with the methods described in Examples 1 and 2 by analogous variants if, instead of 1-(2-chloroethyl)-piperidine hydrochloride, a hydrochloride that is selected according to the desired final compound is used in reaction step c).

As a process for the creation of side chain —X—[CH$_2$]$_n$—Y in the compounds according to the invention, especially also the processes that are described in WO 96/26201 and in WO 93/10741 are suitable.

If X in the desired compounds of general formula I stands for a methylene group, the 2-(4-hydroxyphenyl)-7-(tetrahydropyran-2-yloxy)-3-[4-(tetrahydropyran-2-ylxoy)-phenyl]-2,3-dihydro-4H-1-benzopyran-4-one first obtained as intermediate product in synthesis step c) is converted into the corresponding 2-[(4-trifluoromethylsulfonyloxy)-phenyl] compound. This triflate is palladium(O)-catalyzed, reacted with a compound HC≡C—(CH$_2$)$_{n-1}$—Y (for the meaning of Y, see general formula I) in terms of a Sonogashira coupling [with pyrrolidine as a base, tetrakis (triphenylphosphine)-palladium as a catalyst, with the addition of copper(I) halide, especially -iodide, at an elevated temperature (about 70° C.)], and the α,β-alkyne that is produced is then hydrogenated.

Instead of the compound HC≡C—(CH$_2$)$_{n-1}$—Y, the Sonogashira coupling can also be performed with a o-halogen compound HC≡C—(CH$_2$)$_{n-1}$-Hal (Hal=Cl, Br), and the halide can then be exchanged, before or after the hydrogenation, in base-catalyzed form for the ultimately desired amine radical Z.

As an alternative, the compounds of general formula I, in which X represents a methylene group, can be produced by the reaction sequence that is shown in the diagram below:

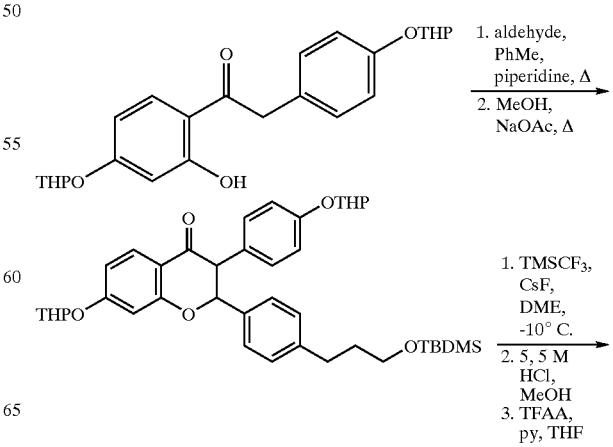

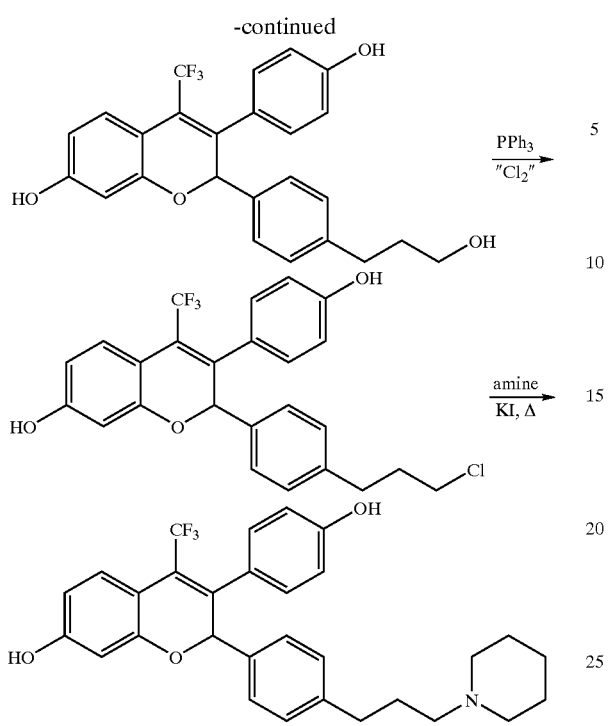

The introduction of fluoroalkyl group Z can be achieved by the addition of this group 4 to the keto group in 4-position with use of a corresponding silyl reagent, for example Me₃Si—Z or with use of a metalted compound M-Z that is capable of nucleophiic addition to a keto group, in which Z is, for example, a lithium atom, a group MgCl— or ZnBr— or ZnI—.

The introduction of a fluoroalkyl group can be illustrated in the following diagram by way of example for the introduction of a pentafluoroethyl group:

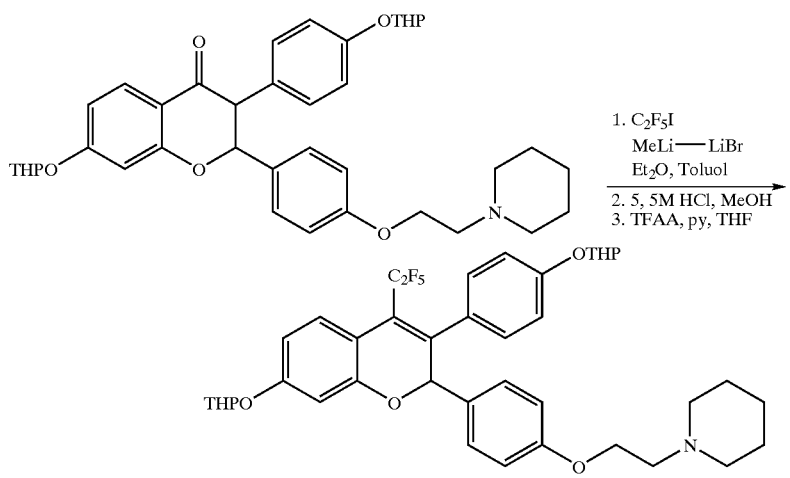

[Key: Toluol = toluene]

To introduce in particular a pentafluoro ethyl group, reference is also made to WO 98/34947. There, for example, in Example 1c), the introduction of a pentafluoroethyl group into 17-position of asteroid is described.

The saponification of ester groupings as well as esterification and etherification of free hydroxy groups is carried out in each case according to established processes of organic chemistry. By observing the different reactivity of the esterified and free 7- and 4'-hydroxy group, the 7,4'-diester can be selectively cleaved and then additionally specifically functionalized.

Monoalkyl ethers can also be separated from the dialkylated compounds by separation of the corresponding alkylation mixture.

The acid addition salts of the compounds of general formula I can also be produced according to conventional processes from the compounds of general formula I.

The examples below are used for a more detailed explanation of the invention without intending that it be limited to these examples.

EXAMPLE 1

(+)-7-Hydroxy-3-(4-hydroxyphenyl)-2-[4-(2-piperidin-1-ylethoxy)-penyl]-4(trifluoromethyl)-2H-1-benzopyran

EXAMPLE 2

(−)-7-Hydroxy-3-(4-hydroxyphenyl)-2-[4-(2-piperidin-1-ylethoxy)-phenyl]-4-(trifluoromethyl)-2H-1-benzopyran a) 1-(2,4-Dihydroxyphenyl)-2-(4-hydroxyphenyl)-ethanone

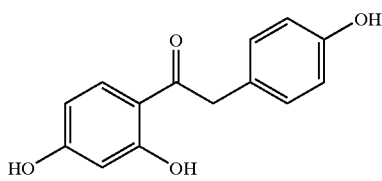

44.6 g (405 mmol) of resorcinol and 67.7 g (445 mmol) of 4-hydroxyphenylacetic acid in 120 ml of toluene are mixed with 150 ml of BF₃OEt₂ and stirred for 3 hours at 100° C. It is allowed to cool off, 200 ml of 12% sodium acetate solution is added at 0–5° C., and it is allowed to stand overnight at room temperature. The crystals are suctioned off and washed twice with 500 ml of water and once with 200 ml of 12% sodium acetate solution. The crystals are allowed to stand overnight again with 600 ml of 12% sodium acetate solution, suctioned off and washed with 300 ml of water. Then, it is recrystallized from 400 ml of ethanol and 1500 ml of water. The crystals are dried at 50° C. in a vacuum. 71.8 g (melting point: 186° C.) accumulates.

b) 1-[2-Hydroxy-4-(tetrahydropyran-2-yloxy)-phenyl]-2-[4-(tetrahydropyran-2-yloxy)-phenyl]-ethanone

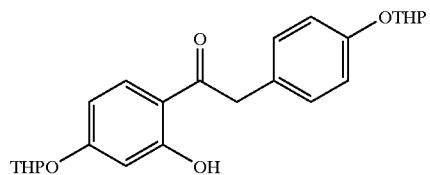

At 0° C., 4.8 mg of p-toluenesulfonic acid is added to 40 g of 1-(2,4-dihydroxyphenyl)-2-(4-hydroxyphenyl)-ethanone in 152 ml of dihydropyran, and it is stirred for 2.5 hours. 100 ml of saturated sodium bicarbonate solution and 250 ml of ethyl acetate are added, the phases are separated, and the aqueous phase is extracted once with 250 ml of ethyl acetate. The combined organic phases are washed once with 80 ml of saturated sodium bicarbonate solution and once with saturated sodium chloride solution, dried on magnesium sulfate and concentrated by evaporation in a rotary evaporator. The residue is mixed with 800 ml of hexane, stirred for 2 hours at room temperature and stored for 20 hours at −20° C. The crystals are suctioned off and resuspended in 400 ml of hexane and stirred for several minutes at room temperature. After being suctioned off once again, 45.3 g of crystals (melting point: 105–106° C.) is obtained.

c) 2-[4-(2-Piperidin-1-ylethoxy)-phenyl]-7-(tetrahydropyran-2-yloxy)-3-[4-(tetrahydropyran-2-yloxy)-phenyl]-2,3-dihydro-4H-1-benzopyran-4-one

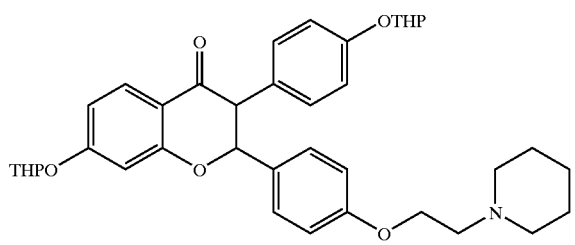

45.3 g of 1-[2-hydroxy-4-(tetrahydropyran-2-yloxy)-phenyl]-2-[4-(tetrahydropyran-2-yloxy)-phenyl]-ethanone, 13.86 g of 4-hydroxybenzaldehyde and 3.55 ml of piperidine in 900 ml of toluene are stirred for 60 hours in a water separator under a nitrogen atmosphere. The cooled solution is concentrated by evaporation in a rotary evaporator. The residue is dissolved in 800 ml of acetone and 50 ml of water and mixed with 24.16 g of 1-(2-chloroethyl)-piperidine hydrochloride and 85.09 g of cesium carbonate. It is stirred under reflux for 19 hours. It is allowed to cool off to room temperature. The precipitate is suctioned off and washed with acetone. The combined filtrates are concentrated by evaporation in a rotary evaporator and purified on silica gel with ethyl acetate/methanol. 33 g is obtained.

d) 4,7-Dihydroxy-3-(4-hydroxyphenyl)-2-[4-(2-piperidin-1-ylethoxy)-phenyl]-4-(trifluoromethyl)-2,3-dihydro-4H-1-benzopyran

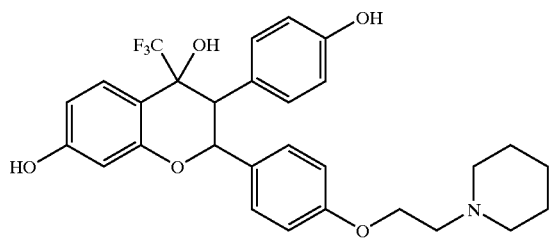

5 g of 2-[4-(2-piperidin-1-ylethoxy)-phenyl]-7-(tetrahydropyran-2-yloxy)-3-[4-(tetrahydropyran-2-yloxy)-phenyl]-2,3-dihydro-4H-1-benzopyran-4-one in 50 ml of ethylene glycol dimethyl ether is mixed with 5 ml of (trifluoromethyl)-trimethylsilane and 150 mg of cesium fluoride, and it is stirred at room temperature. After 48 hours, 2 more ml of (trifluoromethyl)-trimethylsilane and a spatula tip full of cesium fluoride are added. 24 hours later, the volatile components are drawn off in a rotary evaporator. The residue is dissolved in 25 ml of glacial acetic acid and 2.5 ml of water and stirred for 4 hours at 90° C. under an argon atmosphere. After cooling, it is concentrated by evaporation in a rotary evaporator and mixed with 60 ml of ethyl acetate and 30 ml of 10% sodium carbonate solution. After 30 more minutes of stirring at room temperature, the phases are separated and the aqueous phase is shaken out three times with 100 ml of ethyl acetate. The combined organic phases are washed twice with 40 ml of water, dried on magnesium sulfate and concentrated by evaporation. The product is purified on silica gel with dichloromethane/methanol. 1.15 g is obtained.

MS (El, 70 eV, 150° C.): m/e=529 (M$^+$, 0.23%), 511 (M–H$_2$O$^+$, 0.08%).

e) 7-Hydroxy-3-(4-hydroxyphenyl)-2-[4-(2-piperidin-1-ylethoxy)-phenyl]-4-(trifluoromethyl)-2H-1-benzopyran

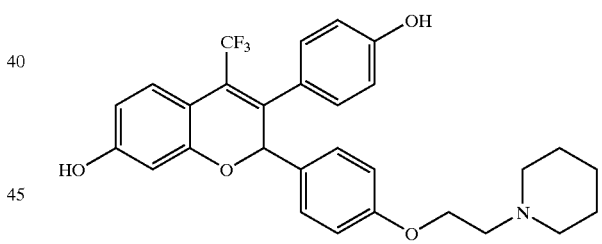

0.88 ml of trifluoroacetic acid anhydride and 1.37 ml of pyridine are simultaneously added in drops to 1.15 g of 4,7-dihydroxy-3-(4-hydroxyphenyl)-2-[4-(2-piperidin-1-ylethoxy) -phenyl]-4-(trifluoromethyl)-2,3-dihydro-4H-1-benzopyran in 20 ml of THF. It is stirred for 4 hours at room temperature before 70 ml of ethyl acetate and 20 ml of 10% sodium carbonate solution are added. It is stirred for 20 more minutes at room temperature. The phases are separated, and the aqueous phase is shaken out three times with 40 ml of ethyl acetate. The combined organic phases are washed twice with 20 ml of water, dried on magnesium sulfate and concentrated by evaporation. The product is prepurified on silica gel with dichloromethane/methanol and then purified with HPLC (nucleosil 50-7, dichloromethane/methanol 85:15, 40 ml/min). 590 mg is obtained.

Then, 825 mg of the racemate is separated with the aid of chiral HPLC (Chiralpak AD 20μ, 250×60 mm, hexane (0.1% triethylamine): ethanol (0.1% triethylamine) 9:1, 90 ml/min).

290 mg is obtained from (+)-enantiomer, and 300 mg is obtained from (−)-enantiomer.

(+)-Enantiomer: [α]D=+279.5° (0.502 in methanol)
(−)-Enantiomer: [α]D=−280° (0.516 in methanol)

EXAMPLE 3

2-[4-(2-Dimethylaminoethoxy)-phenyl]-7-hydroxy-3-(4-hydroxyphenyl)-4 (trifluoromethyl)-2H-1-benzopyran a) 2-[4-Hydroxyphenyl]-7-(tetrahydropyran-2-yloxy)-3-[4-(tetrahydropyran-2-yloxy) -phenyl]-2,3-dihydro-4H-1-benzopyran-4-one

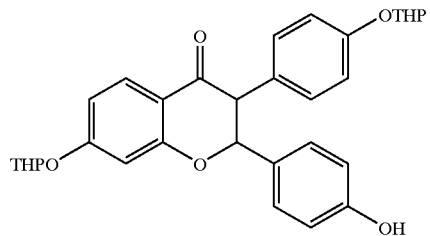

In 20 g of 1-[2-hydroxy-4-(tetrahydropyran-2-yloxy)-phenyl]-2-[4-(tetrahydropyran-2-yloxy)-phenyl]-ethanone, 6.51 g of 4-hydroxybenzaldehyde and 1.44 ml of piperidine in 320 ml of toluene are stirred for 5 hours at a bath temperature of 80° C. and for 30 hours in a water separator under a nitrogen atmosphere. The cooled solution is concentrated by evaporation in a rotary evaporator. The residue is taken up twice in dichloromethane and evaporated to the dry state in a rotary evaporator.

b) 2-[4-(2-Chloroethoxy)-phenyl]-7-(tetrahydropyran-2-yloxy)-3-[4-(tetrahydropyran-2-yloxy)-phenyl]-2,3-dihydro-4H-1-benzopyran-4-one

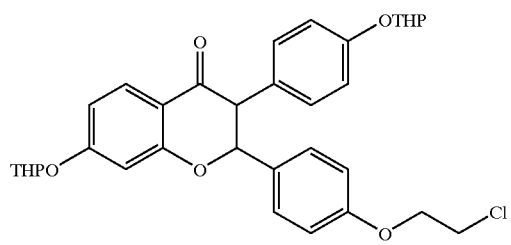

2.19 g of 2-[4-hydroxyphenyl]-7-(tetrahydropyran-2-yloxy)-3-[4-(tetrahydropyran-2-yloxy)-phenyl]-2,3-dihydro-4H-1-benzopyran-4-one, 3.6 g of 1-bromo-2-chloroethane and 2.21 g of potassium carbonate are stirred at a bath temperature of 65° C. overnight in 20 ml of acetone. After cooling, the precipitate is suctioned off and washed with tert-butyl methyl ether. The filtrate is evaporated to the dry state in a rotary evaporator. The residue is chromatographed on silica gel with hexane/ethyl acetate 9:1. 0.838 g of product is obtained.

MS (Cl, NH$_3$, 70 eV, 150° C.): m/e=579 (M+H$^+$, 36.4%), 495 (77.9%), 410 (42.5%).

c) 2-[4-(2-Chloroethoxy)-phenyl]-4,7-dihydroxy-3-(4-hydroxyphenyl)-4-(trifluoromethyl)-2,3-dihydro-4H-1-benzopyran

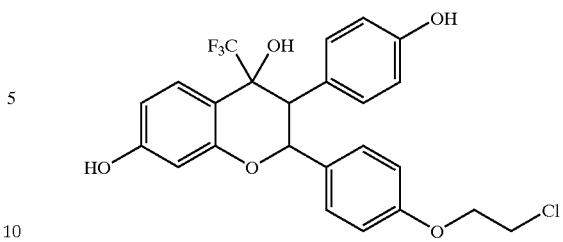

12.7 g of 2-[4-(2-chloroethoxy)-phenyl]-7-(tetrahydropyran-2-yloxy)-3-[4-(tetrahydropyran-2-yloxy)-phenyl]-2,3-dihydro-4H-1-benzopyran-4-one in 120 ml of ethylene glycol dimethyl ether is mixed with 11.5 ml of (trifluoromethyl)-trimethylsilane and 200 mg of cesium fluoride and stirred for 2 hours at −10° C. Then, the reaction solution is poured into 300 ml of saturated sodium chloride solution. It is shaken out three times with 300 ml of ethyl acetate. The combined organic phases are dried on magnesium sulfate and concentrated by evaporation in a rotary evaporator. The accumulating crude product is purified on silica gel with hexane and hexane/ethyl acetate 95:5. 5.7 g is obtained.

2.6 g of 2-[4-(2-chloroethoxy)-phenyl]-7-hydroxy-3-(4-hydroxyphenyl)-4-(trifluoromethyl)-4-(trimethylsiloxy)-2,3-dihydro-4H-1-benzopyran is dissolved in 70 ml of methanol and stirred with 15 ml of 5.5 M HCl for 4 hours at room temperature. The volatile components are drawn off in a rotary evaporator, the remaining residue is mixed with 40 ml of water and extracted three times with 50 ml of dichloromethane. The combined organic phases are washed twice with 40 ml of water, dried on magnesium sulfate and concentrated by evaporation in a rotary evaporator. The residue is purified on silica gel with hexane and hexane/ethyl acetate 8:2. 1.5 g of product is obtained.

MS (EI, 70 eV, 150° C.): m/e=480 (M$^+$, 2.3%), 462 (M−H$_2$O$^+$, 0.3%), 411 (1.2%), 393 (1.3%), 307 (2.8%), 274 (100%).

d) 2-[4-(2-Chloroethoxy)-phenyl]-7-hydroxy-3-(4-hydroxyphenyl)-4-(trifluoromethyl)-2H -1-benzopyran

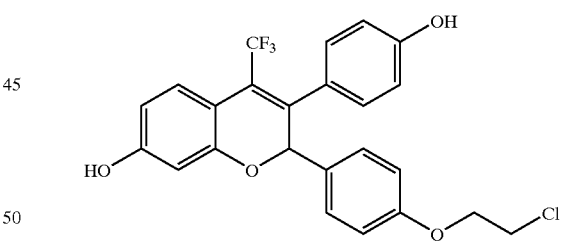

At 0–5° C., 2.87 ml of trifluoroacetic acid anhydride and 3.84 ml of pyridine are simultaneously added in drops to 2.87 g of 2-[4-(2-chloroethoxy)-phenyl]-4,7-dihydroxy-3-(4-hydroxyphenyl)-4-(trifluoromethyl)-2,3-dihydro-4H-1-benzopyran in 60 ml of THF. It is stirred for 3 more hours at room temperature, before 50 ml of saturated sodium chloride solution is added. It is shaken out three times with 50 ml of ethyl acetate. The combined organic phases are washed twice with 40 ml of water, dried on magnesium sulfate and concentrated by evaporation in a rotary evaporator. The remaining residue is purified with hexane and hexane/ethyl acetate 8:2, so that 1.96 g of product is obtained.

MS (El, 70 eV, 150° C.): m/e=462 (M$^+$, 16.5%), 393 (M−CF$_3$$^+$, 63.1%), 369 (43.3%), 307 (100%).

e) 2-[4-(2-Dimethylaminoethoxy)-phenyl]-7-hydroxy-3-(4-hydroxyphenyl)-4-(trifluoromethyl) -2H-1-benzopyran

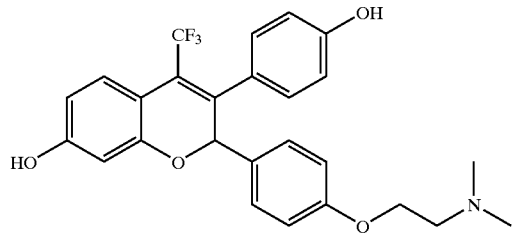

0.035 g of 2-[4-(2-chloroethoxy)-phenyl]-7-hydroxy-3-(4-hydroxyphenyl)-4-(trifluoromethyl)-2H-1-benzopyran in 0.5 ml of 1-methyl-2-pyrrolidone is mixed with 10.4 mg of potassium carbonate, a spatula tip full of potassium iodide and 1 ml of dimethylamine (2M in THF) and stirred at room temperature. After 24 more hours of stirring in each case, 1 ml of dimethylamine solution is added twice. It is stirred for a total of 144 hours. 30 ml of dichloromethane is added, and the organic phase is washed twice with 10 ml of water, dried on magnesium sulfate and concentrated by evaporation in a rotary evaporator. Preparative thin-layer chromatography with dichloromethane/methanol 9:1 yields 15 mg of product.

EXAMPLES 4 TO 16

The other amines (2 molar equivalents) are reacted analogously with 35 mg of 2-[4-(2-chloroethoxy)-phenyl]-7-hydroxy-3-(4-hydroxyphenyl)-4-(trifluoromethyl)-2H-1-benzopyran, whereby the less volatile amines are stirred at 80° C. for 6 hours. For the chromatographic purification, only the ratio of dichloromethane to methanol must be adjusted.

| Examples | Amine | Yield |
| --- | --- | --- |
| 4 | N,N-Diethylamine | 8 mg |
| 5 | N-Methyl-N-phenethylamine | 20 mg |
| 6 | N-Methyl-N-(3-phenylpropyl)amine | 23 mg |
| 7 | N-Butyl-N-ethylamine | 6 mg |
| 8 | Thiomorpholine | 17 mg |
| 9 | Pyrrolidine | 11 mg |
| 10 | Morpholine | 18 mg |
| 11 | N-Methyl-N-pentylamine | 12 mg |
| 12 | N-Isobutyl-N-methylamine | 7 mg |
| 13 | N-Benzyl-N-methylamine | 16 mg |
| 14 | N,N-Dipropylamine | 3 mg |
| 15 | Hexamethylenimine | 8 mg |
| 16 | N-Butyl-N-methylamine | 7.5 mg |

EXAMPLE 17

7-Hydroxy-3-(4-hydroxyphenyl)-2-[4-(3-piperidin-1-ylpropoxy)-phenyl]-4-(trifluoromethyl)-2H-1-benzopyran a) 2-[4-(3-Chloropropoxy)-phenyl]-7-(tetrahydropyran-2-yloxy)-3-[4-(tetrahydropyran-2-yloxy)-phenyl]-2,3-dihydro-4H-1-benzopyran-4-one

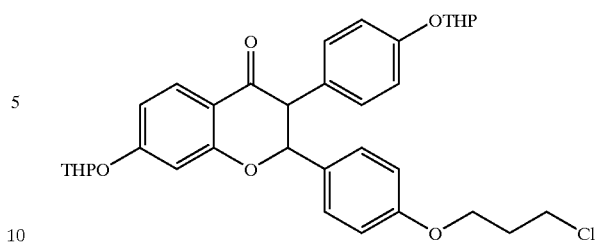

60 g of 2-[4-hydroxyphenyl]-7-(tetrahydropyran-2-yloxy)-3-[4-(tetrahydropyran-2-yloxy) -phenyl]-2,3-dihydro-4H-1-benzopyran-4-one, 91.3 g of 1-bromo-3-chloropropane and 100 g of potassium carbonate are stirred under reflux for 4 hours in 200 ml of acetone. After cooling, the precipitate is suctioned off and washed with acetone. The filtrate is evaporated to the dry state in a rotary evaporator. The residue is chromatographed on silica gel with hexane/ethyl acetate 9:1, 4:1, 3:1 and 7:3. 49.74 g of product is obtained.

MS (Cl, NH$_3$, 70 eV, 150° C.): m/e=593 (M+H$^+$, 35.0%), 509 (17.3%), 425 (6.4%).

b) 2-[4-(3-Chloropropoxy)-phenyl]-4,7-dihydroxy-3-(4-hydroxyphenyl)-4-(trifluoromethyl)-2,3-dihydro-4H-1-benzopyran

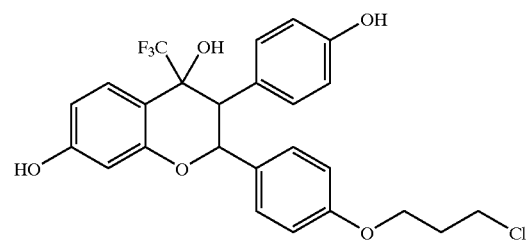

12 g of 2-[4-(3-chloropropoxy)-phenyl]-7-(tetrahydropyran-2-yloxy)-3-[4-(tetrahydropyran-2-yloxy)-phenyl]-2,3-dihydro-4H-1-benzopyran-4-one in 100 ml of ethylene glycol dimethyl ether is mixed with 10.2 ml of (trifluoromethyl)-trimethylsilane and a spatula tip full of cesium fluoride, and it is stirred for 4 hours at −10° C. and for 20 hours at room temperature. Then, the reaction solution is poured into 100 ml of saturated sodium chloride solution. It is shaken out three times with 100 ml of ethyl acetate. The combined organic phases are washed twice with 50 ml of water, dried on magnesium sulfate and concentrated by evaporation in a rotary evaporator. The accumulating crude product is purified on silica gel with hexane and hexane/ethyl acetate 8:2. 8.2 g of product accumulates.

8.2 g of 2-[4-(3-chloropropoxy)-phenyl]-7-hydroxy-3-(4-hydroxyphenyl)-4-(trifluoromethyl)-4-(trimethylsiloxy)-2,3-dihydro-4H-1-benzopyran is dissolved in 100 ml of methanol. At 10–15° C., 40 ml of 5.5 M HCl is slowly added in drops. It is stirred for 4 more hours at room temperature. The volatile components are drawn off in a rotary evaporator, the remaining residue is mixed with 100 ml of water and extracted three times with 100 ml of dichloromethane. The combined organic phases are washed twice with 50 ml of water, dried on magnesium sulfate and concentrated by evaporation in a rotary evaporator. The residue is purified on silica gel with hexane and hexane/ethyl acetate 3:1. 3 g of product is isolated.

c) 2-[4-(3-Chloropropoxy)-phenyl]-7-hydroxy-3-(4-hydroxyphenyl)-4-(trifluoromethyl)-2H-1-benzopyran

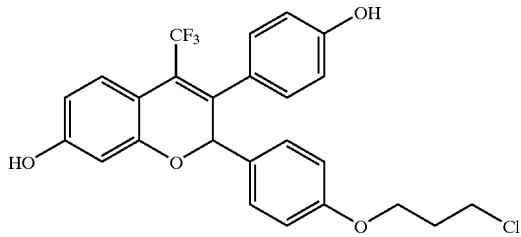

At 0–5° C., 3.34 ml of trifluoroacetic acid anhydride and 3.9 ml of pyridine are simultaneously added in drops to 3 g of 2-[4-(3-chloropropoxy)-phenyl]-4,7-dihydroxy-3-(4-hydroxyphenyl)-4-(trifluoromethyl)-2,3-dihydro-4H-1-benzopyran in 80 ml of THF. It is stirred for 1 hour at 0–5° C. and for 4 more hours at room temperature, before 60 ml of saturated sodium chloride solution is added. After being extracted three times with 80 ml of ethyl acetate, the combined organic phases are washed twice with 50 ml of water, dried on magnesium sulfate and concentrated by evaporation in a rotary evaporator. After chromatographic purification on silica gel with hexane and hexane/ethyl acetate 3:1, the remaining residue yields 1.7 g of product.

MS (EI, 70 eV, 150° C.): m/e=476 ($M^+$, 9.9%), 407 ($M-CF_3^+$, 36.8%), 383 (31.6%), 307 (100%).

d) 7-Hydroxy-3-(4-hydroxyphenyl)-2-[4-(3-piperidin-1-ylpropoxy)-phenyl]-4-(trifluoromethyl)-2H-1-benzopyran

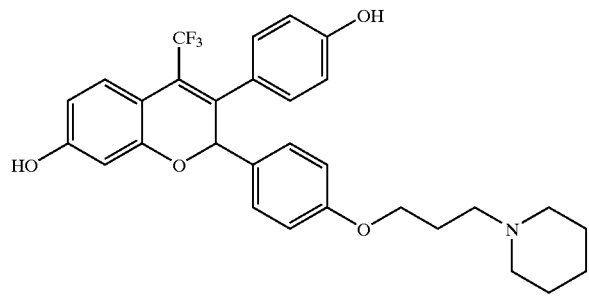

0.035 g of 2-[4-(3-chloropropoxy)-phenyl]-7-hydroxy-3-(4-hydroxyphenyl)-4-(trifluoromethyl)2H-1-benzopyran in 1 ml of 1-methyl-2-pyrrolidone is mixed with 10.1 mg of potassium carbonate, a spatula tip full of potassium iodide and 0.036 ml of piperidine, and it is stirred for 12 hours at 80° C. After 20 ml of ethyl acetate is added, the organic phase is washed three times with 20 ml of water, dried on magnesium sulfate and concentrated by evaporation in a rotary evaporator. The purification of the product by means of preparative HPLC (nucleosil 50-7, dichloromethane/methanol 8:2, 30 ml/min) yields 30 mg of product.

EXAMPLES 18 TO 31

The other amines (5 molar equivalents) are reacted analogously with 35 mg of 2-[4-(2-chloroethoxy)-phenyl]-7-hydroxy-3-(4-hydroxyphenyl)-4-(trifluoromethyl)-2H-1-benzopyran, whereby it is stirred for 22 hours at 80° C. The purification of the products by means of preparative HPLC (nucleosil 50-7, dichloromethane/methanol 7:3, 30 ml/min) yields the products.

| Example | Amine | Yield |
| --- | --- | --- |
| 18 | N,N-Dimethylamine | 20 mg |
| 19 | N,N-Dimethylamine | 9 mg |
| 20 | N-Methyl-N-phenethylamine | 30 mg |
| 21 | N-Methyl-N-(3-phenylpropyl)amine | 30 mg |
| 22 | N-Butyl-N-ethylamine | 23 mg |
| 23 | Thiomorpholine | 30 mg |
| 24 | Pyrrolidine | 25 mg |
| 25 | Morpholine | 24 mg |
| 26 | N-Methyl-N-pentylamine | 22 mg |
| 27 | N-Isobutyl-N-methylamine | 16 mg |
| 28 | N-Benzyl-N-methylamine | 25 mg |
| 29 | N,N-Dipropylamine | 35 mg |
| 30 | Hexamethylenimine | 26 mg |
| 31 | N-Butyl-N-methylamifle | 23 mg |

EXAMPLE 32

7-Hydroxy-3-(4-hydroxyphenyl)-2-[4-(4-piperidin-1-ylbutoxy)-phenyl]-4-(trifluoromethyl -2H-1-benzopyran a) 2-[4-(4-Chlorobutoxy)-phenyl]-7-(tetrahydropyran-2-yloxy)-3-[4-(tetrahydropyran-2-yloxy)-phenyl]-2,3-dihydro-4H-1-benzopyran-4-one

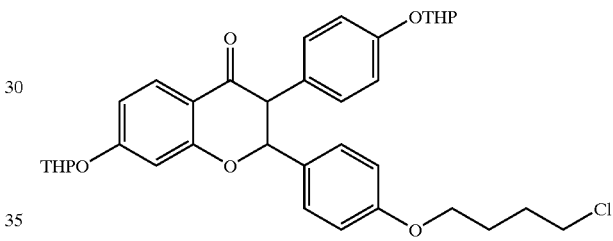

60 g of 2-[4-hydroxyphenyl]-7-(tetrahydropyran-2-yloxy)-3-[4-(tetrahydropyran-2-yloxy) -phenyl]-2,3-dihydro-4H-1-benzopyran-4-one, 99.4 g of 1-bromo-4-chlorobutane and 100 g of potassium carbonate are stirred for 4 hours under reflux in 200 ml of acetone. After cooling, the precipitate is suctioned off and washed with acetone. The filtrate is evaporated to the dry state in a rotary evaporator. The residue is purified on silica gel with hexane/ethyl acetate 9:1, 4:1, 3:1 and 7:3. 22.6 g of product accumulates.

b) 2-[4-(4-Chlorobutoxy)-phenyl]-4,7-dihydroxy-3-(4-hydroxyphenyl)-4-(trifluoromethyl)-2,3-dihydro-4H-1-benzopyran

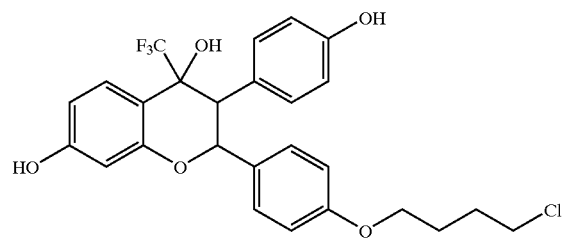

20.4 g of 2-[4-(4-chlorobutoxy)-phenyl]-7-(tetrahydropyran-2-yloxy)-3-[4-(tetrahydropyran-2-yloxy)-phenyl]-2,3-dihydro-4H-1-benzopyran-4-one in 150 ml of ethylene glycol dimethyl ether is mixed with 17 ml of (trifluoromethyl)-trimethylsilane and a spatula tip full of cesium fluoride and stirred for 4 hours at −10° C. and for 20 hours at room temperature. Then, the reaction solution is poured into 10 ml of saturated sodium chloride solution. It is shaken out three times with 100 ml of ethyl acetate. The combined organic phases are washed twice with 50 ml of water, dried on magnesium sulfate and concentrated by evaporation in a rotary evaporator. The accumulating crude product is purified on silica gel with hexane and hexane/ethyl acetate 8:2. 7.8 g of product is isolated.

8.8 g of 2-[4-(4-chlorobutoxy)-phenyl]-7-hydroxy-3-(4-hydroxyphenyl)-4-(trifluoromethyl)-4-(trimethylsilyloxy)-2,3-dihydro-4H-1-benzopyran is dissolved in 100 ml of methanol. 40 ml of 5.5 M HCl is slowly added in drops at 10–15° C. It is stirred for 4 more hours at room temperature. The volatile components are drawn off in a rotary evaporator, the remaining residue is mixed with 100 ml of water and extracted three times with 150 ml of dichloromethane. The combined organic phases are washed twice with 80 ml of water, dried on magnesium sulfate and concentrated by evaporation in a rotary evaporator. After chromatographic purification on silica gel with hexane and hexane/ethyl acetate 3:1, 2.7 g of product accumulates.

c) 2-[4-(4-Chlorobutoxy)-phenyl]-7-hydroxy-3-(4-hydroxyphenyl)-4-(trifuoromethyl)-2H-1-benzopyran

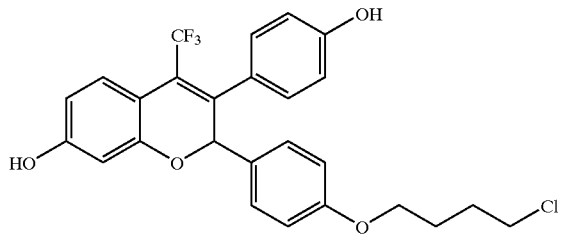

At 0–5° C., 2.92 ml of trifluoroacetic acid anhydride and 3.41 ml of pyridine are simultaneously added in drops to 2.7 g of 2-[4-(4-chlorobutoxy)-phenyl]-4,7-dihydroxy-3-(4-hydroxyphenyl)-4-(trifluoromethyl)-23-dihydro-4H-1-benzopyran in 40 ml of THF. It is stirred for 1 more hour at 0–5° C. and for 2.5 hours at room temperature, before 40 ml of saturated sodium chloride solution is added. It is shaken out three times with 50 ml of ethyl acetate. The combined organic phases are dried on magnesium sulfate and concentrated by evaporation in a rotary evaporator. After chromatographic purification of the residue on silica gel with hexane and hexane/ethyl acetate 3:1, 1.4 g of product accumulates.

MS (El, 70 eV, 150° C.): m/e=490 (M$^+$, 10.1%), 421 (M–CF$_3^+$, 32.0%), 397 (22.0%), 307 (100%).

d) 7-Hydroxy-3-(4-hydroxyphenyl)-2-[4-(4-piperidin-1-ylbutoxy)-phenyl]-4-(trifluoromethyl)-2H-1-benzopyran

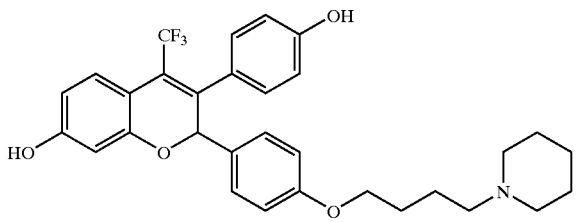

0.036 g of 2-[4-(3-chloropropoxy)-phenyl]-7-hydroxy-3-(4-hydroxyphenyl)-4-(trifluoromethyl)-2H-1-benzopyran in 1 ml of 1-methyl-2-pyrrolidone is mixed with 10.1 mg of potassium carbonate, a spatula tip full of potassium iodide and 0.036 ml of piperidine, and it is stirred for 12 hours at 80° C. After 20 ml of ethyl acetate is added, the organic phase is washed three times with 20 ml of water, dried on magnesium sulfate and concentrated by evaporation in a rotary evaporator. The purification of the product by means of preparative HPLC (nucleosil 50-7, dichloromethane/methanol 8:2, 30 ml/min) yields 26 mg of product.

EXAMPLES 33 TO 46

The other amines (5 molar equivalents) are reacted analogously with 36 mg of 2-[4-(2-chloroethoxy)-phenyl]-7-hydroxy-3-(4-hydroxyphenyl)-4-(trifluoromethyl)-2H-1-benzopyran, whereby it is stirred for 22 hours at 80° C. The purification of the products by means of prpparative HPLC (nucleosil 50-7, dichloromethane/methanol 7:3, 30 ml/minute) yields the products.

| Example | Amine | Yield |
|---|---|---|
| 33 | N,N-Dimethylamine | 20 mg |
| 34 | N,N-Diethylamine | 9 mg |
| 35 | N-Methyl-N-phenethylamine | 23 mg |
| 36 | N-Methyl-N-(3-Phenylpropyl)amine | 23 mg |
| 37 | N-Butyl-N-ethylamine | 18 mg |
| 38 | Thiomorpholine | 28 mg |
| 39 | Pyrrolidine | 27 mg |
| 40 | Morpholine | 18 mg |
| 41 | N-Methyl-N-pentylamine | 27 mg |
| 42 | N-Isobutyl-N-methylamine | 17 mg |
| 43 | N-Benzyl-N-methylamine | 24 mg |
| 44 | N,N-Dipropylamine | 13 mg |
| 45 | Hexamethylenimine | 25 mg |
| 46 | N-Butyl-N-methylamine | 22 mg |

EXAMPLE 47

(+)-7-Methoxy-3-(4-methoxyphenyl)-2-[4-(2-piperidin-1-ylethoxy)-phenyl]-4-(trifluoromethyl)-2H-1-benzopyran

EXAMPLE 48

(−)-7-Methoxy-3-(4-methoxyphenyl)-2-[4-(2-piperidin-1-ylethoxy)-phenyl]-4-(trifluoromethyl)-2H-1-benzopyran a) 2-[4-(2-Chloroethoxy)-phenyl]-7-methoxy-3-(4-methoxyphenyl)-4-(trifluoromethyl)-2H-1-benzopyran

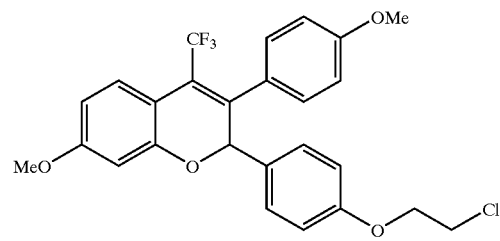

170 mg of 2-[4-(2-chloroethoxy)-phenyl]-7-hydroxy-3-(4-hydroxyphenyl)-4-(trifluoromethyl)-2H-1-benzopyran in 5 ml of acetone is mixed with 0.0297 ml of methyl iodide and 101 mg of potassium carbonate and stirred overnight at room temperature. The reaction mixture is poured into dilute sodium chloride solution and extracted three times with ethyl acetate. The combined organic phases are washed once with water and once with saturated sodium chloride solution, dried on magnesium sulfate and concentrated by evaporation in a vacuum. The purification is carried out on preparative thin-layer plates with hexane/ethyl acetate 1:1. 52 mg of product is isolated.

b) 7-Methoxy-3-(4-methoxyphenyl)-2-[4-(2-piperidin-1-ylethoxy)-phenyl]-4-(trifluoromethyl)-2H-1-benzopyran

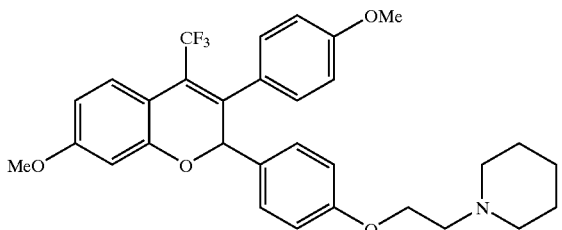

125 mg of 2-[4-(2-chloroethoxy)-phenyl]-7-methoxy-3-(4-methoxyphenyl)-4-(trifluoromethyl)-2H-1-benzopyran and 12.5 mg of potassium iodide are stirred in 2.5 ml of piperidine for 18 hours at 100° C. The cooled solution is poured into dilute sodium chloride solution, the aqueous phase is extracted three times with ethyl acetate, and the combined organic phases are dried on magnesium sulfate and concentrated by evaporation in a vacuum. The product is purified on analytical thin-layer plates with dichloromethane/methanol 9:1. 86 mg of product accumulates, which is separated in the enantiomers with the aid of chiral HPLC (Chiralpak AD 10μ, 250×60 mm, hexane (0.1% triethylamine); ethanol (0.1% triethylamine) 9:1, 90 ml/minute).

22 mg is obtained from (+)-enantiomer, and 30 mg is obtained from (−)-enantiomer.

(+)-Enantiomer: [α]D=+286.00 (0.48 in CHCl₃)

(−)-Enantiomer: [α]D −241.90 (0.54 in CHCl₃)

EXAMPLE 49

7Hydroxy-3-(4-hydroxyphenyl)-2-[4-(3-piperidin-1-1-1-thiapropyl)-phenyl]-4-(trifluoromethyl)-2H-1-benzopyran a) 4-(Methylsulfinyl)-benzaldehyde

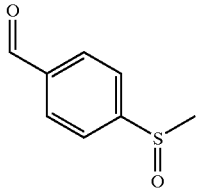

At 0° C., 16.19 g of 3-chloroperbenzoic acid (70%) is added to 10.52 g of 4-methylthio-benzaldehyde in 197 ml of chloroform. After 1 hour at 0° C., 7.30 g of calcium hydroxide is added. It is heated to room temperature and stirred for 30 more minutes at room temperature. The suspension is suctioned off and washed twice with dichloromethane. The combined organic phases are evaporated to the dry state and purified on silica gel with dichloromethane, dichloromethane/methanol 99:1, 98:2 and 97:3. 9.14 g of white solid accumulates.

b) 4-Mercaptobenzaldehyde

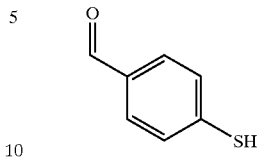

4.8 g of 4-(methylsulfinyl)-benzaldehyde is dissolved in 50 ml of trifluoroacetic anhydride and stirred for 30 minutes under reflux. The highly volatile components are drawn off, and the residue is added to 200 ml of triethylamine, to which then 200 more ml of methanol is added. It is thoroughly stirred briefly, and then the highly volatile components are drawn off. The residue is diluted with dichloromethane, washed twice with saturated ammonium chloride solution, dried on magnesium sulfate and concentrated by evaporation in a rotary evaporator. 4.52 g of yellow solid accumulates.

c) 4-(3-Chloro-1-thiapropyl)-benzaldehyde

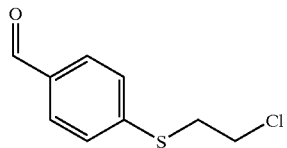

4.51 g of 4-mercaptobenzaldehyde in 43.8 ml of acetonitrile is mixed with 7.00 g of potassium carbonate and 11.8 ml of 1-bromo-2-chloroethane and stirred for 4 hours at 90° C. It is diluted with ethyl acetate, and washed twice with water and once with saturated sodium chloride solution. The combined organic phases are dried on magnesium sulfate and concentrated by evaporation. The crude product is purified on silica gel with hexane, hexane/ethyl acetate 95:5, 90:10 and 85:15. 3.88 g of yellow liquid is obtained.

d) 2-[4-(3-Chloro-1-thiapropyl)-phenyl]-7-(tetrahydropyran-2-yloxy)-3-[4-(tetrahydropyran-2-yloxy)-phenyl]-2,3-dihydro-4H-1-benzopyran-4-one

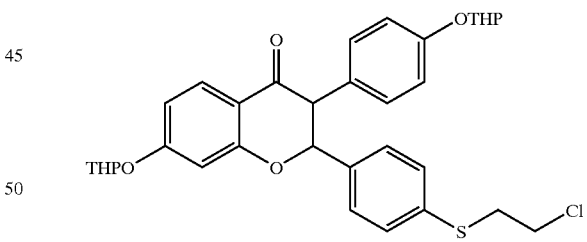

0.65 ml of piperidine is added to 8.91 g of 1-[2-hydroxy-4-(tetrahydropyran-2-yloxy)-phenyl]-2-[4-(tetrahydropyran-2-yloxy)-phenyl]-ethanone and 4.77 g of 4-(3-chloro-1-thiapropyl)-benzaldehyde in 78.6 ml of toluene. It is stirred for 5.5 hours under reflux in a water separator. The solution is cooled and evaporated to the dry state. The crude product is purified on silica gel with hexane and hexane/ethyl acetate 95:5, 90:10, 85:15, 80:20, 75:25 and 70:30. 1.512 g of the product accumulates as a yellow foam. In addition, 3.70 more g of the corresponding chalcone is isolated, which is converted into the product after the subsequent procedure. At room temperature, 4.69 g of the chalcone is dissolved in 205 ml of methanol and mixed with 32.05 g of sodium acetate. It is stirred for 6 hours at a bath temperature of 100° C. After cooling, the solvent is drawn off in a rotary evaporator, the residue is poured into water and extracted three times with ethyl acetate. The combined organic phases are washed twice with water, dried on magnesium sulfate and concentrated by evaporation in a rotary evaporator. Column-chromatographic purification on silica gel with hexane and hexane/ethyl acetate 9:1, 8:2, 7:3 and 6:4 yields 1.408 g of a light foam.

MS (Cl, NH$_3$, 70 eV, 150° C.): m/e 595 (M+H, 18.7%), 511 (20.9%).

e) 2-[4-(3-Chloro-1-thiapropyl)-phenyl]-4,7-dihydroxy-3-(4-hydroxyphenyl)-4-(trifluoromethyl)-2,3-dihydro-4H-1-benzopyran

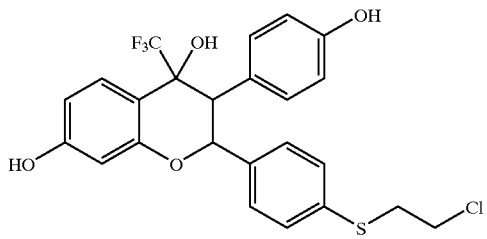

At –10° C., 2.54 ml of (trifluoromethyl)-trimethylsilane and 31.2 mg of cesium fluoride are added to 2.04 g of 2-[4-(3-chloro-1-thiapropyl)-phenyl]-7-(tetrahydropyran-2-yloxy)-3-[4-(tetrahydropyran-2-yloxy)-phenyl]-2,3-dihydro-4H-1-benzopyran-4-one in 19.6 ml of ethylene glycol dimethyl ether, and it is stirred for 1 hour at –10° C. Then, the reaction solution is poured into ml of saturated sodium chloride solution. It is shaken out three times with ether. The combined organic phases are dried on magnesium sulfate and concentrated by evaporation in a rotary evaporator. The accumulating crude product is purified on silica gel with hexane and hexane/ethyl acetate 95:5, 90:10 and 85:15. 0.825 g is obtained.

0.811 g of 2-[4-(3-chloro-1-thiapropyl)-phenyl]-7-hydroxy-3-(4-hydroxyphenyl)-4-(trifluoromethyl)-(trimethylsiloxy)-2,3-dihydro-4H-1-benzopyran is dissolved in 21.8 ml of methanol and stirred with 6.2 ml of 5.5 M HCl for 0.5 hour at room temperature. The volatile components are drawn off in a rotary evaporator, the remaining residue is added to water and extracted three times with dichloromethane. The combined organic phases are washed twice with water, dried on magnesium sulfate and concentrated by evaporation in a rotary evaporator. The residue is purified on silica gel with hexane and hexane/ethyl acetate 9:1, 8:2, 7:3, 6:4 and 1:1. 448 mg of product is obtained.

MS (El, 70 eV, 150° C.): m/e=496 (M$^+$, 4.2%), 427 (M–CF$_3^+$, 1.1%), 409 (1.2%), 290 (100%).

f) 2-[4-(3-Chloro-1-thiapropyl)-phenyl]-7-hydroxy-3-(4-hydroxyphenyl)-4-(trifluoromethyl)-2H-1-benzopyran

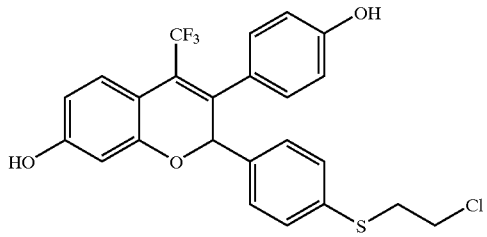

In the ice bath, 0.501 ml of trifluoroacetic acid anhydride and 0.723 ml of pyridine are simultaneously added in drops to 448 mg of 2-[4-(3-chloro-1-thiapropyl)-phenyl]-4,7-dihydroxy-3-(4-hydroxyphenyl)-4-(trifluoromethyl)-2,3-dihydro-4H-1-benzopyran in 9.09 ml of THF. It is stirred for 2.5 more hours at room temperature before being poured into saturated sodium chloride solution. It is shaken out three times with ethyl acetate. The combined organic phases are dried on magnesium sulfate and concentrated by evaporation in a rotary evaporator. The remaining residue is purified on silica gel with hexane/ethyl acetate 7/3. 415 mg of product accumulates.

MS (El, 70 eV, 150° C.): m/e=478 (M$^+$, 12.9%), 409 (M–CF$_3^+$, 24.6%), 385 (16.4%), 307 (100%).

g) 7-Hydroxy-3-(4-hydroxyphenyl)-2-[4-(3-piperidin-1-yl-1-thiapropyl)-phenyl]-4-(trifluoromethyl)-2H-1-benzopyran

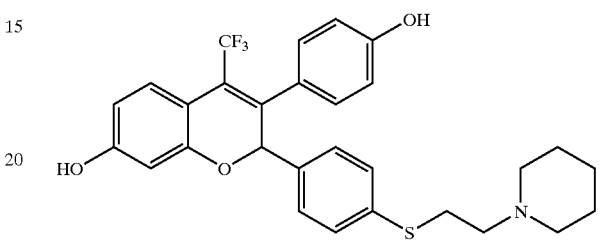

220 mg of 2-[4-(3-chloro-1-thiapropyl)-phenyl]-7-hydroxy-3-(4-hydroxyphenyl)-4-(trifluoromethyl)-2H-1-benzopyran in 2 ml of piperidine is mixed with 42.7 mg of potassium iodide and stirred for 6 hours at 100° C. After cooling, it is poured into water and shaken out three times with ethyl acetate. The combined organic phases are washed twice with water, dried on magnesium sulfate and concentrated by evaporation in a rotary evaporator. The purification of the product is carried out on silica gel with dichloromethane/methanol-9:1. 274 mg of product accumulates.

MS (El, 70 eV, 150° C.): m/e=527 (M$^+$, 0.8%), 307 (1.9%).

Additional thia compounds according to the invention can be produced by an analogous procedure by a longer α,ω-dihaloalkane being used in stage c).

What is claimed is:
1. A compound formula I

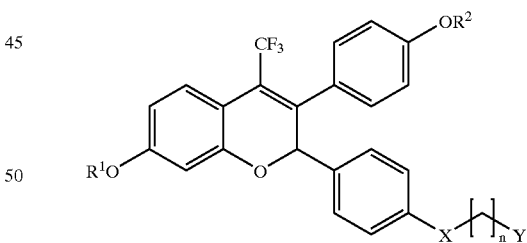

wherein
R$^1$ and R$^2$, independently of one another, mean a hydrogen atom, a straight-chain or branched-chain C$_2$-C$_5$ alkyl group, a methyl group, a straight-chain or branched-chain alkanoyl group with up 1 to 5 carbon atoms or a benzoyl group, X means an oxygen or a sulfur atom or a methylene group, n means 2, 3or4, Y is a piperidine, pyrrolidine, hexamethyleneimino, dimethylamino, diethylamino, dipropylamino, N-methyl-N-phenethylamino, N-methyl-N-(3-phenylpropyl)amino, N-butyl-N-ethylamino, thiomorpholino, morpholino, N-methyl-N- pentylamino, N-isobutyl-N-methylamino, N-benzyl-N-methylamino, or N-butyl-N-methylamino radical,
or Y means a group -NR$^3$R$^4$, wherein
R$^3$ and R$^4$, independently of one another, mean a hydrogen atom,
a monofluoromethyl, difluoromethyl, trifluoromethyl, pentafluoroethyl, 2,2,2-trifluoroethyl, 4,4,4-trifluorobutyl, 3,3,4,4,4-pentafluorobutyl, 4,4,5,5,5-yentafluoropentyl, or nonafluorobutyl group, a physiologically compatible addition salt with an organic or an inorganic acid.

2. A compound formula I according to claim 1 in the form of a racemate.

3. A compound of formula I according to claim 1 in the form of a separate optical isomer.

4. A compound of formula I according to claim 1, wherein R$^1$ and/or R$^2$ is hydrogen.

5. A compound of formula I according to claim 1, wherein R$^1$ and/or R$^2$ is a pivaloyl radical.

6. A compound of formula I according to claim 1, wherein R$^1$ and/or R$^2$ is a methyl radical.

7. A compound according to claim 1, wherein X is an oxygen atom.

8. A compound according to claim 1, wherein X is a sulfur atom.

9. A compound according to claim 1, wherein X is a methylene group.

10. A compound according to claim 1, wherein n has the value of 2.

11. A compound according to claim 1, wherein n has the value of 3.

12. A compound according to claim 1, wherein n has the value of 4.

13. A compound to claim 1, wherein Y is a piperidine radical.

14. A compound according to claim 1, wherein Y is a pyrrolidine radical.

15. A compound according to claim 1, wherein Y is a hexamethyleneimino radical.

16. A compound according to claim 1, wherein Y is a dimethylamino group.

17. A compound according to claim 1, wherein Y is a diethylamino group.

18. A compound according to claim 1, wherein Y is a dipropylamino group.

19. A compound according to claim 1, wherein Y is an N-methyl-N-phenethylamino group.

20. A compound according to claim 1, wherein Y is an N-methyl-N-(3-phenylpropyl)amino group.

21. A compound according to claim 1, wherein Y is an N-butyl-N-ethylamino group.

22. Compound according to claim 1, wherein Y is a thiomorpholino group.

23. A compound according to claim 1, wherein Y is a morpholino group.

24. A compound according to claim 1, wherein Y is an N-methyl-N-pentylamino group.

25. A compound according to claim 1, wherein Y is an N-isobutyl-N-methylamino group.

26. A compound according to claim 1, wherein Y is an N-benzyl-N-methylamino group.

27. A compound according to claim 1, wherein Y is an N-butyl-N-methylamino group.

28. A compound according to claim 1, in the form of a hydrochloride.

29. A pharmaceutical composition comprising at least one compound or salt of formula I according to claim 1 in a pharmaceutically effective amount and a pharmaceutically acceptable carrier.

30. A compound, which is:

(+)-7-hydroxy-3-(4'-hydroxyphenyl)-2-[4"-(2'"-piperidin-1-yletoxy)phenyl]-4-(trifluoromethyl)-2H-1-benzopyran, (−)-7-hydroxy-3-(4'-hydroxyphenyl)-2-[4"-(2'"-piperidin-1-yletoxy)phenyl]-4-(trifluoromethyl)-2H-1-benzopyran, (+)-7-pivaloyloxy-3-(4'-pivaloyloxyphenyly)-4-trifluoromethyl-2-(4'-(2-'"-piperidinoethoxy)phenyl)-2H-benzopyran, (−)-7-pivaloyloxy-3-(4'-pivaloyloxyplenyl)-4-trifluoromethyl-2-(4'-(2'"-piperidinoethoxy)phenyl)-2H-benzopyran, 2-[4"-(2'"-dimethylaminoethoxy)phenyl]-7-hydroxy-3-(4'-hydronxphenyl)-4-(trifluoromethyl)-2H-1-benzopyran, 2-[4"-(2'"-diethylaminoethoxy)phenyl]-7-hydroxy-3-(4'-hydroxyphenyl)-4-(trifluoromethyl)-2H-1-benzopyran, 7-hydroxy-3-(4'-hydroxyphenyl)-2-[4"-(2'"-N-methyl-N-phenethylaminoethoxy)phenyl]-4-(trifluoromethyl)-2H-1-benzopyran, 7-hydroxy-3-(4'-hydroxyphenyl)-2-{4"-[2'"-N-methyl-N-(3'"-phenylpropyl)aminoethoxy]phenyl}-4-(trifluoromethyl)-2H-1-benzopyran, 2-[4"-(2'"-N-butyl-N-methylaniinoethoxy)phenyl]-7-hydroxy-3-(4'-hydroxyphenyl)-4-(trifluoromethyl)-2H-1-benzopyran, 7-hydroxy-3-(4'-hydroxyphenyl)-2-[4"-morpholin-1-ylethoxy)phenyl]-4-(trifluoromethyl)-2H-1-benzopyran, 7-hydroxy-3-(4'-hydroxyphenyl)-2-[4"-(2'"-pyrrolidin-1-ylethoxy)phenyl]-4-(trifluoromethyl)-2H-1-benzopyran, 7-hydroxy-3-(4'-hydroxyphenyl)-2-[4"-(2'"-morpholin-1-ylethoxy)phenyl]-4-(trifluoromethyl)-2H-1-benzopyran, 7-hydroxy-3-(4'-hydroxyphenyl)-2-[4"-(2'"-N-methyl-pentylaminoethoxy)phenyl]4-(trifluoromethyl)-2H-1-benzopyran, 7-hydroxy-3-(4'-hydroxyphenyl)-2-[4"-(2'"-N-isobutyl-N-methylaminoethoxy)phenyl]4-(trifluoromethyl)-2H-1-benzopyran, 2-[4"-(2'"-N-benzyl-N-methylaminoethoxy)phenyl]-7-hydroxyl-3-(4'-hydroxyphenyl)-4-(trifluoromethyl)-2H-1-benzopyran, 2-[4"-(2'"-N,N-di-n-propylaminoethoxy)phenyl-]-7-hydroxy-3-(4'-hydronxphenyl)-4-(trifluoromethyl)-2H-1-benzopyran, 2-[4"-(2'"-hexamethylenimin-1-ylethoxy)phenyl]-7-hydroxy-3-(4'-hydroxyphenyl)-4-(trifluoromethyl)-2H-1-benzopyran, 2-[4"-(2'"-N-butyl-N-ethylaminoedoxy)phenyl]-7-hydroxy-3-(4'-hydronxphenyl)-4-(trifluoromethyl)-2H-1-benzopyran, 7-hydroxy-3-(4'-hydroxyphenyl)-2-[4"-(3'"-piperidin-1-ylpropoxy)phenyl]-4-(trifluoromethyl)-2H-1-benzopyran, 2[4"-(3'"-N-dimethylaminopropoxy)phenyl]-7-hydroxy-3-(4'-hydroxyphenyl)-4-(trifluoromethyl)-2H-1-benzopyran, 2-[4"-(3'"-N-diethylaminopropoxy)phenyl]-7-hydroxy-3-(4'-hydroxyphenyl-4-(trifluoromethyl)-2H-1-benzopyran, 7-hydroxy-3-(4'-hydroxyphenyl)-2-[4"-(3'"-N-methyl-N-phenethylaminopropoxy)phenyl]-4-(trifluoromethyl)-2H-1-benzopyran, 7-hydroxy-3-(4'-hydroxyphenyl)-2-{4"-[3'"-N-methyl-N-(3""-phenylpropyl)aminopropoxy]phenyl}-4-(trifluoromethyl)-2H-1-benzopyran, 2-[4"-(3'"-N-butyl-N-ethylaminoprppoxyl)phenyl]-7-hydroxy-3-(4'-hydroxyphenyl) -4-(trifluoromethyl)-2H-1-benzopyran, 7-hydroxy-3-(4'-hydroxyphenyl)-2-[4'-(3'"-thiomorpholino-1-ylpropoxy)phenyl]-4-(trifluoromethyl)-2H-1-benzopyran, 7-hydroxy-3-(4'-hydroxyphenyl)-2-[4"-(3'"-pyrrolidin-1-ylpropoxy)phenyl]-4-(trifluoromethyl)-2H-1-benzopyran, 7-hydroxy-3-(4'-hydroxyphenyl)-2-[4"-(3'"-morpholin-1-ylpropoxy)phenyl]-4-(trifluoromethyl)-2H-1-benzopyran, 7-hydroxy-3-(4'-hydroxyphenyl)-2-[4'-(3'"-N-methyl-N-pentylaminopropoxy)phenyl]-4-(trifluoromethyl)-2H-1-benzopyran, 7-hydroxy-3-(4'-hydroxyphenyl)-2-[4'-(3'"-N-isobutyl-N-pentylaminopropoxy)phenyl]-4-4-(trifluoromethyl)-2H-1-benzopyran, 2-[4"-(3'"-N-benzyl-N-methylaminopropoxy)phenyl]-7-hydroxy-3-(4'-hydroxyphenyl) -4-(trifluoromethyl)-2H-1-benzopyran, 2-[4"-(3'"-N,N-di-n-propylanlinopropoxy)phenyl]-7-hydroxy-3-(4'-hydroxyphenyl) -4-(trifluoromethyl)-2H-1-benzopyran, 2-[4"-(3'"-hexamethylenimin-1-ylpropoxy)phenyl]-7-hydroxy-3-(4'-hydroxyphenyl) -4-(trifluoromethyl)-2H-1-benzopyran, 2-[4"-(3'"-N-butyl-N-methylaminopropoxy)phenyl]-7-hydroxy-3-(4'-hydroxyphenyl) -4-(trifluoromethyl)-2H-1-benzopyran, 7-hydroxy-3-(4'-hydroxyphenyl)-2-[4"-(4'"-piperidin-1-ylbutoxy)phenyl]-4-(trifluoromethyl)-2H-1-benzopyran, 2-[4"-(4'"-N-dimethylaminobutoxy)phenyl]-7-hydroxy-3-(4'-hydroxyphenyl) -4-(trifluoramethyl)-2H-1-benzopyran, 2-[4"-(4'"-N-diethylaminobutoxy)phenyl]-7-hydroxy-3-(4'-hydroxyphenyl) -4-(trifluoromethyl)-2H-1-benzopyran, 7-hydroxy-3-(4'-hydroxyphenyl)-2-[4"-(4'"-N-methyl-N-pentylaminobutoxy)phenyl]-4-(trifluoromethyl)-2H-1-benzopyran, 7-hydroxy-3-(4'-hydroxyphenyl)-2-{4"-[4'"-N-methyl-N-(3""-phenylpropyl)aminobutoxy]phenyl}-4-(trifluoromethyl)-2H-1-benzopyran, 2-[4"-(4'"-N-butyl-N-ethylaminobutoxy)phenyl]-7-hydroxy-3-(4'-hydroxyphenyl)-4-(trifluoromethyl)-2H-1-benzopyran, 7-hydroxy-3-(4'-hydroxyphenyl)-2-[4"-(4'"-thiomorpholino-1-ylbutoxy)phenyl]-4-(trifluoromethyl)-2H-1-benzopyran, 7-hydroxy-3-(4'-hydroxyphenyl)-2-[4"-(4'"-pyrrolidin-1-ylbutoxy)phenyl]-4-(trifluoromethyl)-2H-1-benzopyran, 7-hydroxy-3-(4'-hydroxyphenyl)-2-[4"-(4'"-morpholin-1-ylbutoxy)phenyl]-4-(trifluoromethyl)-2H-1-benzopyran, 7-hydroxy-3-(4'-hydroxyphenyl)-2-[4"-(4'"-N-methyl-N-pentylaminobutaxy)phenyl]-4-(trifluoromethyl)-2H-1-benzopyran, 7-hydroxy-3-(4'-hydroxyphenyl)-2-[4"-(4'"-N-isobutyl-N-pentylaminobutoxy)phenyl]-4-(trifluoromethyl)-2H-1-benzopyran, 2-[4"-(4'"-N-benzyl-N-methylaxninobutoxy)phenyl]-7-hydroxy-3-(4'-hydroxyphenyl) -4-(trifluoromethyl)-2H-1-benzopyran, 2-[4"-(4'"-N,N-di-n-propylaminobutoxy)phenyl]-7-hydroxy-3-(4'-hydroxyphenyl) -4-(trifluoromethyl)-2H-1-benzopyran, 2-[4"-(4'"-hexamethylenimin-1-ylbutoxy)phenyl]-7-hydroxy-3-(4'-hydroxyphenyl)-4-(trifluoromethyl)-2H-1-benzopyran, 2-[4"-(4'"-N-butyl-N-methylaminobutoxy)phenyl]-7-hydroxy-3-(4'-hydroxyphenyl) -4-(trifluoromethyl)-2H-1-benzopyran, (+)-7-mehoxy-3-(4'-mehoxyphenyl)-2-[4"-(2'"-pipexidin-1-ylethoxy)phenyl]-4-(trifluoromethyl)-2H-1-benzopyran, (−)-7-mehoxy-3-(4'-mehoxyphenyl)-2-[4"-(2'"-pipexidin-1-ylethoxy)phenyl]-4-(trifluoromethyl)-2H-1-benzopyran, or 7-hydroxy-3-(4'-hydroxyphenyl)-2-[4"-(3'"-piperidin-1-yl-1-thiapropyl)phenyl ]-4-(trifluoromethyl)-2H-1-benzopyran.

31. A compound according to claim 30, in the form of a racemate.

32. A compound according to claim 30, in the form of a separate optical isomer.

33. A compound according to claim 30, in the form of a hydrochloride.

34. A pharmaceutical product comprising at least one compound according to claim 30, in a pharmaceutically effective amount, and a pharmaceutically acceptable carrier.

35. A method of treating an estrogen-dependent disease or tumor; providing a hormone replacement therapy; treating hair loss, diffuse alopecia or hirsutism; treating endometriosis or endometrial carcinoma; providing birth control; treating osteoporosis; treating rheumatoid arthritis; or treating Alzheimer's disease or other neurodegenerative diseases, comprising administering an effective amount of a compound according to claim 1 to a patient in need thereof.

36. A method of treating an estrogen-dependent disease or tumor; providing a hormone replacement therapy; treating hair loss, diffuse alopecia or hirsutism; treating endometriosis or endometrial carcinoma; providing birth control; treating osteoporosis; treating rheumatoid arthritis; or treating Alzheimer's disease or other neurodegenerative diseases, comprising administering an effective amount of a compound according to claim 30, to a patient in need thereof.

* * * * *

UNITED STATES PATENT AND TRADEMARK OFFICE
CERTIFICATE OF CORRECTION

PATENT NO. : 6,844,336 B2
DATED : January 18, 2005
INVENTOR(S) : Kuenzer et al.

It is certified that error appears in the above-identified patent and that said Letters Patent is hereby corrected as shown below:

Title page,
Item [54], Title, reads "ANTI-ESTOGENIC" should read -- ANTI-ESTROGENIC --.

Column 28,
Line 42, reads "compound formula" should read -- compound of formula --.
Line 59, reads "with up 1 to 5 carbon" should read -- with 1 to 5 carbon --.
Line 62, reads "3or4," should read -- 3 or 4, --.

Column 29,
Line 5, reads "and $R^4$,independently" should read -- and $R^4$, independently --.
Line 10, reads "yentafluoropentyl," should read -- pentafluoropentyl, --.
Line 10, reads "group," should read -- group, or --.
Line 13, reads "compound formula" should read -- compound of formula --.
Line 52, reads "Compound" should read -- A compound --.

Column 30,
Line 10, reads "pivaloyloxyphenyly)" should read -- pivaloyloxyphenyl) --.
Line 11, reads "(4'-(2-'''-" should read -- (4"-(2'''- -- .
Line 13, reads "pivaloyloxyplenyl)" should read -- pivaloyloxyphenyl) --.
Line 14, reads "(4'-(2'''-" should read -- (4"-(2'''- --.
Line 17, reads "hydronxphenyl)" should read -- hydroxyphenyl) --.
Line 26, reads "(3'''-phenylpropyl)" should read -- (3""-phenylpropyl) --.
Line 28, reads "methylaniinoethoxy)" should read -- ethylaminoethoxy) --.
Line 31, reads "morpholin" should read -- thiomorpholin --.
Line 40, reads "N-methyl-" should read -- N-methyl-N- --.
Lines 41 and 44, reads "phenyl]4" should read -- phenyl]-4 --.
Line 47, reads "hydroxyl" should read -- hydroxy --.
Line 49, reads "phenyl-]" should read -- phenyl] --.
Line 50, reads "hydronxphenyl" should read -- hydroxyphenyl --.
Line 55, reads "ethylaminoedoxy" should read -- methylaminoethoxy --.
Line 56, reads "hydronxphenyl" should read -- hydroxyphenyl --.
Line 62, reads "2[4"" should read -- 2-[4" --.
Line 66, reads "hydroxyphenyl-4" should read -- hydroxyphenyl)-4 --.

UNITED STATES PATENT AND TRADEMARK OFFICE
CERTIFICATE OF CORRECTION

PATENT NO. : 6,844,336 B2
DATED : January 18, 2005
INVENTOR(S) : Kuenzer et al.

It is certified that error appears in the above-identified patent and that said Letters Patent is hereby corrected as shown below:

Column 31,
Line 7, reads "ethylaminoprppoxyl" should read -- ethylaminopropoxy --.
Line 10, reads "[4'-(3'''-" should read -- [4"-(3'''- --.
Line 11, reads "thiomorpholino" should read -- thiomorpholin --.
Line 20, reads "[4'-(3'''-" should read -- [4"-(3'''-" --.
Line 23, reads "[4'-(3'''-" should read -- [4"-(3'''-" --.
Line 24, reads "pentylaminopropoxy" should read -- methylaminopropoxy --.
Line 24, reads "phenyl]-4-4-(" should read -- phenyl]-4-( --.
Line 29, reads "propylanlinopropoxy" should read -- propylaminopropoxy --.
Line 43, reads "trifluoramethyl" should read -- trifluoromethyl --.
Line 59, reads "thiomorpholino" should read -- thiomorpholin --.

Column 32,
Line 8, reads "pentylaminobutaxy" should read -- pentylaminobutoxy --.
Line 13, reads "methylaxninobutoxy" should read -- methylaminobutoxy --.
Line 25, reads "mehoxy-3-(4'-mehoxyphenyl" should read -- methoxy-3-(4'-methoxyphenyl --.
Line 25, reads "pipexidin" should read -- piperidin --.
Line 28, reads "mehoxy-3-(4'-mehoxyphenyl" should read -- methoxy-3-(4'-methoxyphenyl --.
Line 28, reads "pipexidin" should read -- piperidin --.

Signed and Sealed this

First Day of November, 2005

JON W. DUDAS
*Director of the United States Patent and Trademark Office*